US008003617B2

(12) United States Patent  
Cheng et al.

(10) Patent No.: US 8,003,617 B2
(45) Date of Patent: Aug. 23, 2011

(54) METHODS OF TREATING DIABETES MELLITUS

(75) Inventors: Seng H. Cheng, Wellesley, MA (US); Nelson S. Yew, Upton, MA (US); Ronald K. Scheule, Hopkinton, MA (US); Hongmei Zhao, Northborough, MA (US)

(73) Assignee: Genzyme Corporation, Cambridge, MA (US)

(*) Notice: Subject to any disclaimer, the term of this patent is extended or adjusted under 35 U.S.C. 154(b) by 888 days.

(21) Appl. No.: 11/667,224

(22) PCT Filed: Nov. 9, 2005

(86) PCT No.: PCT/US2005/040596
§ 371 (c)(1),
(2), (4) Date: Sep. 11, 2007

(87) PCT Pub. No.: WO2006/053043
PCT Pub. Date: May 18, 2006

(65) Prior Publication Data
US 2008/0161379 A1  Jul. 3, 2008

Related U.S. Application Data

(60) Provisional application No. 60/626,448, filed on Nov. 10, 2004.

(51) Int. Cl.
- *A61K 31/70* (2006.01)
- *A61K 31/685* (2006.01)
- *A61K 31/535* (2006.01)
- *A61K 31/42* (2006.01)
- *A61K 31/40* (2006.01)
- *A61K 31/195* (2006.01)
- *A61K 31/16* (2006.01)
- *A61K 31/155* (2006.01)

(52) U.S. Cl. ...... 514/35; 514/78; 514/231.2; 514/233.8; 514/236.2; 514/380; 514/422; 514/428; 514/561; 514/625; 514/629; 514/635; 514/866

(58) Field of Classification Search ........... 514/35, 514/233.8, 231.2, 236.2, 422, 428, 380, 561, 514/625, 635, 629, 866, 78
See application file for complete search history.

(56) References Cited

U.S. PATENT DOCUMENTS

| | | | |
|---|---|---|---|
| 4,065,562 A | 12/1977 | Ohata et al. |
| 4,182,767 A | 1/1980 | Murai et al. |
| 4,533,668 A | 8/1985 | Matsumura et al. |
| 4,639,436 A | 1/1987 | Junge et al. |
| 5,041,441 A | 8/1991 | Radin et al. |
| 5,302,609 A | 4/1994 | Shayman et al. |
| 5,472,969 A | 12/1995 | Platt et al. |
| 5,525,616 A | 6/1996 | Platt et al. |
| 5,631,394 A | 5/1997 | Wei et al. |
| 5,707,649 A | 1/1998 | Inokuchi et al. |
| 5,763,438 A | 6/1998 | Inokuchi et al. |
| 5,849,326 A | 12/1998 | Inokuchi et al. |
| 5,907,039 A | 5/1999 | Jinbo et al. |
| 5,916,911 A | 6/1999 | Shayman et al. |
| 5,945,442 A | 8/1999 | Shayman et al. |
| 5,952,370 A | 9/1999 | Shayman et al. |
| 5,972,928 A | 10/1999 | Chatterjee |
| 6,030,995 A | 2/2000 | Shayman et al. |
| 6,040,332 A | 3/2000 | Shayman et al. |
| 6,051,598 A | 4/2000 | Shayman et al. |
| 6,228,889 B1 | 5/2001 | Chatterjee |
| 6,255,336 B1 | 7/2001 | Shayman et al. |
| 6,335,444 B1 | 1/2002 | Jinbo et al. |
| 6,511,979 B1 | 1/2003 | Chatterjee |
| 6,569,889 B2 | 5/2003 | Shayman et al. |
| 6,610,703 B1 | 8/2003 | Jacob et al. |
| 6,660,749 B2 | 12/2003 | Butters et al. |
| 6,835,831 B2 | 12/2004 | Hirth |
| 6,855,830 B2 | 2/2005 | Hirth et al. |
| 6,890,949 B1 | 5/2005 | Shayman et al. |
| 6,916,802 B2 | 7/2005 | Shayman et al. |
| 7,148,251 B2 | 12/2006 | Shayman |
| 7,196,205 B2 | 3/2007 | Siegel et al. |
| 7,253,185 B2 | 8/2007 | Shayman et al. |
| 7,265,228 B2 | 9/2007 | Hirth et al. |
| 7,335,681 B2 | 2/2008 | Shayman et al. |
| 2001/0003741 A1 | 6/2001 | Masuda et al. |
| 2002/0156107 A1 | 10/2002 | Shayman et al. |
| 2002/0198240 A1 | 12/2002 | Shayman et al. |
| 2003/0050299 A1 | 3/2003 | Hirth et al. |
| 2003/0073680 A1 | 4/2003 | Shayman et al. |
| 2004/0260099 A1 | 12/2004 | Shayman |
| 2005/0009872 A1 | 1/2005 | Hirth et al. |
| 2005/0049235 A1 | 3/2005 | Shayman et al. |

(Continued)

FOREIGN PATENT DOCUMENTS

EP  0126974 A1  12/1984

(Continued)

OTHER PUBLICATIONS

International Search Report and Written Opinion for PCT/US2005/0405967, mailed Jun. 27, 2006 from the International Searching Authority of the European Patent Office.

Jimbo et al., "Development of a New Inhibitor of Glucosylceramide Synthase[1]," J. Biochem 127:485-491, 2000.

Lee et al., "Improved Inhibitors of Glucosylceramide Synthase," J. Bio. Chem. 274:14662-14669, 1999.

Seibutsu Yuki Kagaku Kenkyusho KK, Database Accession No. XP-002372073, Derwent Publications Ltd., Aug. 27, 2003.

Jankowski, K., "Microdetermination of phosphorus in organic materials from polymer industry by microwave-induced plasma atomic emission spectrometry after microwave digestion", *Microchem. J.*, 70:41-49, 2001.

International Preliminary Report on Patentability for International Application No. PCT/US2008/011450 dated Apr. 7, 2010.

(Continued)

*Primary Examiner* — Kevin E Weddington
(74) *Attorney, Agent, or Firm* — Hamilton, Brook, Smith & Reynolds, P.C.

(57) ABSTRACT

The invention provides methods of treating a diabetic subject comprising administering a glucosylceramide synthase inhibitor to the subject.

50 Claims, 16 Drawing Sheets

U.S. PATENT DOCUMENTS

| | | |
|---|---|---|
| 2005/0222244 A1 | 10/2005 | Siegel et al. |
| 2005/0239862 A1 | 10/2005 | Shayman et al. |
| 2005/0267094 A1 | 12/2005 | Shayman et al. |
| 2006/0058349 A1 | 3/2006 | Ali et al. |
| 2006/0074107 A1 | 4/2006 | Butters et al. |
| 2006/0217560 A1 | 9/2006 | Shayman |
| 2007/0066581 A1 | 3/2007 | Aerts |
| 2007/0072916 A1 | 3/2007 | Shayman |
| 2007/0112028 A1 | 5/2007 | Orchard |
| 2007/0203223 A1 | 8/2007 | Siegel et al. |
| 2008/0146533 A1 | 6/2008 | Shayman et al. |
| 2009/0312392 A1 | 12/2009 | Shayman et al. |
| 2010/0256216 A1 | 10/2010 | Siegel et al. |

FOREIGN PATENT DOCUMENTS

| | | |
|---|---|---|
| EP | 0 144 290 A2 | 6/1985 |
| EP | 1 384 719 A1 | 1/2004 |
| EP | 1 528 056 A1 | 5/2005 |
| EP | 1576894 A1 * | 9/2005 |
| GB | 2054371 | 2/1981 |
| JP | 35-5798 | 5/1960 |
| JP | 9-169664 | 6/1997 |
| JP | 9216856 A1 | 8/1997 |
| JP | 10-324671 | 12/1998 |
| JP | 10338636 A | 12/1998 |
| JP | 2003 238410 A | 8/2003 |
| WO | WO 97/10817 | 3/1997 |
| WO | WO 98/52553 | 11/1998 |
| WO | WO 01/04108 A1 | 1/2001 |
| WO | WO 01/80852 A1 | 11/2001 |
| WO | WO 02/50019 A2 | 6/2002 |
| WO | WO 02/055498 A1 | 7/2002 |
| WO | WO 02/062777 A2 | 8/2002 |
| WO | WO 03/008399 A | 1/2003 |
| WO | WO 03/057874 A1 | 7/2003 |
| WO | WO 03/068255 A1 | 8/2003 |
| WO | WO 2004/007453 A1 | 1/2004 |
| WO | WO 2004056748 A1 * | 7/2004 |
| WO | WO 2004/078193 A1 | 9/2004 |
| WO | WO 2005/039578 A2 | 5/2005 |
| WO | WO 2005/040118 A1 | 5/2005 |
| WO | WO 2005/063275 A1 | 7/2005 |
| WO | WO 2005087023 A1 * | 9/2005 |
| WO | WO 2005/108600 A1 | 11/2005 |
| WO | WO 2005/123055 A2 | 12/2005 |
| WO | WO 2006/053043 A2 | 5/2006 |
| WO | WO 2006/053043 A3 | 5/2006 |
| WO | WO 2007/022518 A1 | 2/2007 |
| WO | WO 2007/134086 A2 | 11/2007 |
| WO | WO 2007/134086 A3 | 11/2007 |
| WO | WO 2008/011478 A2 | 1/2008 |
| WO | WO 2008/011487 A2 | 1/2008 |
| WO | WO 2008/012555 A2 | 1/2008 |
| WO | WO 2008/150486 A2 | 12/2008 |
| WO | WO 2009/045503 A1 | 4/2009 |
| WO | WO 2009/117150 | 9/2009 |

OTHER PUBLICATIONS

International Preliminary Report on Patentability for International Application No. PCT/US2009/001773 dated Sep. 21, 2010.

Abe, A., et al., "Structural and stereochemical studies of potent inhibitors of glucosylceramide synthase and tumor cell growth," *J. of Lipid Research*, 36:611-621 (1995).

Abe, A., et al., "Induction of Glucosylceramide Synthase by Synthase Inhibitors and Ceramide," *Biochim. Biophys. Acta*, 1299: 333-341 (1996).

Abe, A., et al., "Metabolic Effects of Short-Chain Ceramide and Glucosylceramide on Sphingolipids and Protein Kinase C," *Eur. J. Biochem*, 210: 765-773 (1992).

Abe, A., et al., "Improved Inhibitors of Glucosylceramide Synthase," *J. Biochem.*, 111:191-196 (1992).

Abdel-Magid, A., et al., "Metal-Assisted Aldol Condensation of Chiral α-Halogenated Imide Enolates: A Stereocontrolled Chiral Epoxide Syntheses,"*J. Am. Chem Soc.*, 108: 4595-4602 (1986).

Adams, L.A., et al., "Nonalcoholic Fatty Liver Disease," *CMAJ*, 172(7):899-905 (2005).

Alberti, C., "Chloramphenicol. XII and XIII. Chloramphenicol analogs. p-Nitrophenyldiaminopropanols", *Chemical Abstracts Service*, XP002495477 retrieved from CAPLUS Database accession No. 1957:17088 (abstract).

Alker, D., et al., "Application of Enantiopure Templated Azomethine Ylids to β-Hydroxy-α-amino Acid Syntheses," *Tetrahedron*, 54: 6089-6098 (1998).

Alon, R., et al., "Glycolipid Ligands for Selectins Support Leukocyte Tethering and Rolling Under Physiologic Flow Conditions," *J. Immunol.*, 154: 5356-5366 (1995).

Ames, Bruce N., "Assay of Inorganic Phosphate, Total Phosphate and Phosphatases," *Methods Enzymol.*, 8: 115-118 (1996).

Asano, N., "Glycosidase Inhibitors: Update and Perspectives on Practical Use," *Glycobiology*, 13(10):93R-104R (2003).

Bielawska, A., et al., "Ceramide-Mediated Biology: Determination of Structural and Stereospecific Requirements Through the Use of N-Acyl-Phenylaminoalcohol Analogs," *J. Biol. Chem.*, 267: 18493-18497 (1992).

Bielawska, et al., "Modulation of Cell Growth and Differentiation by Ceramide," *FEBS Letters*, 307(2): 211-214 (1992).

Blobe, G.C., et al., "Regulation of Protein Kinase C and its Role in Cancer Biology," *Cancer Metastasis Rev.*, 13: 411-431 (1994).

Brenkert, A., et al., "Synthesis of Galactosyl Ceramide and Glucosyl Ceramide by Rat Brain: Assay Procedures and Changes with Age," *Brain Res.*, 36: 183-193 (1972).

Caplus Listing of Accession No: 1985:221199, Keith McCullagh, et al., "Carboxyalkyl peptide derivatives."

Carson, K.G., et al., "Studies on Morpholinosphingolipids: Potent Inhibitors of Glucosylceramide Synthase," *Tetrahedron Letters*, 35(17): 2659-2662 (1994).

Chatterjee, S., et al., "Oxidized Low Density Lipoprotein Stimulates Aortic Smooth Muscle Cell Proliferation," *Glycobiology*, 6(3):303-311 (1996).

Chatterjee, S., et al., "Role of Lactosylceramide and MAP kinase in the proliferation of proximal tubular cells in human polycystic kidney disease," *Journal of Lipid Research*, 37(6):1334-1344 (1996).

Clark, J.M., et al., "Nonalcoholic Fatty Liver Disease, An Underrecognized Cause of.Cryptogenic Cirrhosis," *JAMA*, 289(22):3000-3004 (2003).

Communication from European Patent Office for EP Patent Application No. 05 826 118.1-1216, dated Aug. 13, 2007, including copy of a partial preliminary examination report.

Zhao, H., et al., "Inhibiting Glycosphingolipid Synthesis Improves Glycemic Control and Insulin Sensitivity in Animal Models of Type 2 Diabetes," *Diabetes*, 56(5):1210-1218 (2007).

Comuzzie, A.G., et al., "The Baboon as a Nonhuman Primate Model for the Study of the Genetics of Obesity," *Obesity Research*, 11(1):75-80 (2003).

Dellaria, Jr., J.F., et al., "Enantioselective Synthesis of α-Amino Acid Derivatives via the Stereoselective Alkylation of a Homochiral Glycine Enolate Synthon," *J. Org. Chem.*, 54: 3916-3926 (1989).

Dickie, P., et al., "HIV-Associated Nephropathy in Transgenic Mice Expressing HIV-1 Genes," *Virology*, 185:109-119 (1991).

Dittert, L.W., et al., "Acetaminophen Prodrugs I-Synthesis, Physicochemical Properties and Analgesic Activity", *J. Pharm. Sci.* 57(5), pp. 774-780 (1968).

Elbein, A.D., "Glycosidase Inhibitors: Inhibitors of N-linked Oligosaccharide Processing," *The FASEB Journal*, 5:3055-3063 (1991).

European Search Report, European Application No. 09003291.3 Apr. 29, 2009.

Evans, D.A., et al., "Stereoselective Aldol Condensations Via Boron Enolates," *J. Am. Chem. Soc.*, 103: 3099-3111 (1981).

Fan, J-G., et al., "Preventie Effects of Metformin on Rats with Nonalcoholic Steatohepatitis," *Hepatology*, 34(4)(1), p. 501A (2003).

Felding-Habermann, B., et al., "A Ceramide Analog Inhibits T Cell Proliferative Response Through Inhibition of Glycosphingolipid Synthesis and Enhancement of N,N-Dimethylsphingosine Synthesis," *Biochemistry*, 29: 6314-6322 (1990).

Folch, J., et al., "A Simple Method for the Isolation and Purification of Total Lipides from Animal Tissues," *J. Biol. Chem.*, 226:497-509, 1957.

Freireich, E., et al., "Quantitative Comparison of Toxicity of Anticancer Agents in Mouse, Rat, Hampster, Dog, Monkey, and Man", Cancer Chemother. Reports 50(4):219 (1966).

Gatt, S., et al., "Assay of Enzymes of Lipid Metabolism with Colored and Fluorescent Derivatives of Natural Lipids," Meth. Enzymol., 72: 351-375 (1981).

Gill-Randall, R.J., et al., "Is human Type 2 diabetes maternally inherited? Insights from an animal model," Diabet. Med. 21 (7):759 (2004).

Hakomori, S. "New Directions in Cancer Therapy Based on Aberrant Expression of Glycosphingolipids: Anti-adhesion and Ortho-Signaling Therapy," Cancer Cells 3:461-470 (1991).

Hammett, L.P. Physical Organic Chemistry, (NY: McGraw), (1940).

Harwood, L.M., et al., "Double diastereocontrol in the synthesis of enantiomerically pure polyoxamic acid," Chem. Commun., 2641-2642 (1998).

Harwood, L.M., et al., "Asymmetric Cycloadditions of Aldehydes to Stabilized Azomethine Ylids: Enantiocontrolled Construction of β-Hydroxy-α-amino acid Derivitives," Tetrahedron: Asymmetry, 3(9): 1127-1130 (1992).

Högberg, T., et al., "Theoretical and Experimental Methods in Druge Design Applied on Antiphyshotic Dopamine Antagonists." In Textbook of Drug Design and Development, pp. 55-91 (1991).

Hospattankar, A.V., et al., "Changes in Liver Lipids After Administration of 2-Decanoylamino-3-morpholinopropiophenone and Chlorpromazine," Lipids, 17(8): 538-543 (1982).

Inokuchi, et al., "Amino Alcohol Esters as Ceramide Analogs and Pharmaceuticals Containing Them for Treatment of Nerve Diseases," Abstract of CAPLUS Accession No. 1998: 786189, JP 10324671 (1998).

Inokuchi, et al., (1996): SNT International CAPLUS database, Columbus (OH), accession number: 1996: 214749.

Inokuchi, J., et al., "Preparation of the Active Isomer of 1-phenyl-2-decanoylamino-3-morpholino-1-propanol, Inhibitor of Murine Clucocerebroside Synthetase," Journal of Lipid Research, 28:565-571 (1987).

Inokuchi, J., et al., "Antitumor Activity Via Inhibition of Glycosphingolipid Biosynthesis," Cancer Lett., 38:23-30 (1987).

Inokuchi, J., et al., "Inhibition of Experimental Metastasis of Murine Lewis Lung Carcinoma by an Inhibitor of Glucosylceramide Synthase and Its Possible Mechanism of Action," Cancer Research, 50:6731-6737 (1990).

Zador, I., et al., "A Role for Glycosphingolipid Accumulation in the Renal Hypertrophy of Streptozotocin-induced Diabetes Mellitus," J. Clin. Invest., 91:797-803 (1993).

Yamashita, T., et al., "Enhanced Insulin Sensitivity in Mice Lacking Ganglioside GM3," Proc. Natl. Acad. Sci., 100(6):3445-3449 (2003).

Inokuchi, K., et al., "Aminoalcohol Derivatives for Treatment of Abnormal Proliferative Diseases," Chemical Abstracts Service, XP002495476 retrieved from CAPLUS Database Accession No. 1998:816280 (abstract).

International Preliminary Examination Report on Patentability, issued in International Application PCT/US2000/18935 (WO 01/04108) dated Jul. 20, 2001.

International Preliminary Report on Patentability for International Application No. PCT/US2002/022659 dated Jul. 24, 2003.

Ziche, M., et al., "Angiogenesis Can Be Stimulated or Repressed In Vivo by a Change in GM3:GD3 Ganglioside Ratio," Lab. Invest., 67:711-715 (1992).

International Preliminary Report on Patentability issued in International Application No. PCT/US2007/068521, dated Nov. 11, 2008, with Written Opinion.

International Preliminary Report on Patentability, issued in International Application PCT/US2002/00808, dated Jan. 1, 2003.

International Preliminary Report on Patentability, issued in International Application PCT/US2005/040596 dated May 15, 2007, including copy of Written Opinion.

International Search Report for PCT/US2000/018935 dated Nov. 28, 2000.

International Search Report for PCT/US2002/00808 dated Oct. 1, 2002.

International Search Report for PCT/US2002/022659 dated Nov. 5, 2002.

Jaffrézou, Jr., et al., "Inhibition of Lysosomal Acid Sphingomyelinase by Agents which Reverse Multidrug Resistance," Biochim. Biophys. Acta, 1266: 1-8 (1995).

Jaffrézou, Jr., et al., "Inhibition of Lysosomal Acid Sphingomyelinase by Agents which Reverse Multidrug Resistance," Biochim. Biophys. Acta, 1266: 1-8 (1995).

Kabayama, K., et al., "TNFα-induced Insulin Resistance in Adipocytes as a Membrane Microdomain Disorder: Involvement of Ganglioside GM3," Glycobiology, 15(1):29-29 (2005).

Kalén, A., et al., "Elevated Ceramide Levels in $GH_4C_1$ Cells Treated with Retinoic Acid," Biochim. Biophys. Acta, 1125: 90-96 (1992).

Kopaczyk, K., C., et al., "In Vivo Conversions of Cerebroside and Ceramide in Rat Brain," J. Lipid Res., 6: 140-145 (1965).

Kurosawa, M., et al., $^{14}$C-Labeling of novel Atypical β-Adrenoceptor Agonist, SM-11044, Journal of Labelled Compounds and Radiopharmaceuticals, 38(3): 285-297 (1996).

Harwood Academic, "Theoretical and Experimental Methods in Drug Design Applied on Antipsychotic Dopamine Antagonists" Textbook of Drug Design and Development, pp. 55-91 (1991).

Masson, E., et al., "a-Series Gangliosides Mediate the Effects of Advanced Glycation End Products on Pericyte and Mesangial Cell Proliferation-A Common Mediator for Retinal and Renal Microangiopathy?," Diabetes, 54:220-227 (2005).

Mitchell, S., et al., "Glycosyltransferase Inhibitors: Synthesis of D-threo-PDMP, L-threo-PDMP, and Other Brain Glucosylceramide Synthase Inhibitors from D- or L-Serine," J. Org. Chem., 63: 8837-8842 (1998).

Miura, T., et al., "Synthesis and Evaluation of Morpholino- and Pyrrolidinosphingolipids as Inhibitors of Glucosylceramide Synthase", Bioorganic and Medicinal Chemistry, (6) 1481-1489 (1998).

Nakamura, K., et al., "Coomassie Brilliant Blue Staining of Lipids on Thin-Layer Plates," Anal. Biochem., 142: 406-410 (1984).

Nicolaou, K., et al., "A Practical and Enantioselective Synthesis of Glycosphingolipids and Related Compounds. Total Synthesis of Globotriasylceramide (Gb3)," J. Am. Chem., Soc., 110: 7910-7912 (1988).

Nishida, A., et al., "Practical Synthesis of threo-(1S, 2S)- and erythro-(1R, 2S)-1-Phenyl-2-palmitoylamino-3-morpholino-1-propanol (PPMP from L-Serine,"Synlett, 389-390(1998).

Nojiri, H., et al., "Ganglioside GM3: An acidic membrane component that increases during macrophage-like cell differentiation can induce monocytic differentiation of human myeloid and monoctyoid leukemic cell lines HL-60 and U937,"Proc. Natl. Acad. Sci., 83:782-786 (1986).

Notification Concerning Transmittal of International Preliminary Report on Patentability for International Application No. PCT/US2008/006906 dated Dec. 10, 2009.

Notification of Office Action for European Patent Office for EP Patent Application No. 05 826 118.1-1216, dated Nov. 13, 2007.

Notification of Transmittal of International Search Report and The Written Opinion of the International Searching Authority dated Nov. 21, 2007, issued in International Application No. PCT/US2007/068521.

Notification of Transmittal of the International Preliminary Report on Patentability of the International Searching Authority from counterpart International Application No. PCT/US2008/006906 dated Dec. 10, 2009.

Notification of Transmittal of the International Search Report and Written Opinion of the International Searching Authority from counterpart International Application No. PCT/US2008/011450 dated Jan. 21, 2009.

Notification of Transmittal of the International Search Report and Written Opinion of the International Searching Authority from counterpart International Application No. PCT/US2009/001773 dated Nov. 11, 2009.

Notification of Transmittal of the International Search Report and Written Opinion of the International Searching Authority from counterpart International Application No. PCT/US2009/051864 dated Nov. 3, 2009.

Notification of Transmittal of the International Search Report and Written Opinion of the International Searching Authority from counterpart International Application No. PCT/US2009/005435 dated Feb. 12, 2010.

Ogawa, S., et al., "Synthesis and Biological Evaluation of Four Stereoisomers of PDMP-Analogue, N-(2-Decylamino-3-Hydroxy-3-Phenylprop-1-YL)-β-Valienamine, and Related Compounds," *Bioorganic & Medicinal Chemistry Letters*, 7(14):1915-1920 (1997).

Overkleeft, H.S., et al., "Generation of Specific Deoxynojirimycin-type Inhibitors of the Non-lysosomal Glucosylceramidase," *The Journal of Biological Chemistry*, 273(41):26522-26527 (1998).

Preiss, J., et al., "Quantitative Measurement of *sn*-1,2-Diaelglycerols Present in Platelets, Hepatocytes, and *ras*-and *sis*-Transformed Normal Rat Kidney Cells," *J. Biol.Chem.*, 261(19): 8597-8600 (1986).

Radin, N. S., "Killing Cancer Cells by Poly-drug Elevation of Ceramide Levels, A Hypothesis Whose Time has Come:," *Eur. J. Biochem.* 268(2): 193-204 (2001).

Radin, N. S., et al., "Metabolic Effects of Inhibiting Glucosylceramide Synthesis with PDMP and Other Substances."*Advances in Lipid Research: Sphingolipids, Part B.*, R.M. Bell et al., Eds. (San Diego: Academic Press), 26: 183-213 (1993).

Radin, N. S., et al., "Ultrasonic Baths as Substitutes for Shaking Incubator Baths," *Enzyme*, 45: 867-70 (1991).

Radin, N. S., et al., "Use of an Inhibitor of Glucosylceramide Synthesis, D-1-Phenyl-2-decanoylamino-3-morpholino-1-propanol," In *NeuroProtocols: a Companion to Methods in Neurosciences*, S.K. Fisher, et al., Eds., (San Diego: Academic Press) 3: 145-155 (1993).

Rosenweld, A.G., et al., "Effects of the Glucosphingolipid Synthesis Inhibitor, PDMP, on Lysosomes in Cultured Cells," *J. Lipid Res.*, 35: 1232-1240 (1994).

Rosenweld, A.G., et al., "Effects of a Sphingolipid Synthesis Inhibitor on Membrane Transport Through the Secretory Pathway," *Biochemistry*, 31: 3581-3590 (1992).

Rubino, MD, F., et al., "Letter to the Editor," *Annals of Surgery*, 240(2):389-390 (2004).

Sandhoff, K., et al., "Biosynthesis and Degradation of Mammalian Glycosphingolipids," *Phil. Trans. R. Soc. Lond*, B 358:847-861 (2003).

Sasaki, A., et al., "Overexpression of Plasma Membrane-Associated Sialidase Attenuates Insulin Signaling in Transgenic Mice," *The Journal of Biological Chemistry*, 278(30):27896-27902 (2003).

Shayman, J.A., et al., "Glucosphingolipid Dependence of Hormone-Stimulated Inositol Trisphophate Formation," *J. Biol. Chem.*, 265(21): 12135-12138 (1990).

Shayman, J.A., et al., "Modulation of Renal Epithelial Cell Growth by Glucosylceramide," *The Journal of Biological Chemistry*, 266(34):22968-22974 (1991).

Shukla, A., et al., "Metabolism of D-[$^3$H]*threo*-1-phenyl-2-decanoylamino-3-morpholino-l-propanol, an inhibitor of glucosylceramide synthesis and the synergistic action of an inhibitor of microsomal momooxygenase," *J. of Lipid Research*, 32: 713-722 (1991).

Shukla, G.S., et al., "Glucosylceramide Synthase of Mouse Kidney: Further Characterization with an Improved Assay Method," *Arch. Biochem. Biophys.*, 283(2): 372-378 (1990).

Shukla, G., et al., "Rapid Kidney Changes Resulting From Glycosphingolipid Depletion by Treatment with a Glucosyltransferase Inhibitor," *Biochim. Biophys. Acta*, 1083: 101-108 (1991).

Skehan, P., et al., "New Colorimetric Cytotoxicity Assay for Anticancer-Drug Screening," *N. Natl. Cancer Inst.*, 82(13): 1107-1112 (1990).

Strum, J.C., et al.,"1-β-D-Arabinofuranosylcytosine Stimulates Ceramide and Diglyceride Formation in HL-60- Cells," *J. Biol. Chem.*, 269(22): 15493-15497 (1994).

Svensson, M., et al., "Epithelial Glucosphingolipid Expression as a Determinant of Bacterial Adherence and Cytokine Production," *Infection and Immunity*, 62(10):4404-4410 (1994).

Tagami, S., et al., "Ganglioside GM3 Participates in the Pathological Conditions of Insulin Resistance," *The Journal of Biological Chemistry*, 227(5):3085-3092 (2002).

Tang, W., et al., "Phorbol Ester Inhibits 13-Cis-Retinoic Acid-Induced Hydrolysis of Phosphatidylinositol 4,5-Biophosphate in cultured Murine Keratinocytes: A Possible Negative Feedback Via Protein Kinase C-Activation," *Cell Bioch. Funct.*, 9: 183-191 (1991).

Uemura, K., et al, "Effect of an Inhibitor of Glucosylceramide Synthesis on Cultured Rabbit Skin Fibroblasts," *J Biochem.*, (Tokyo) 108(4): 525-530 (1990).

Vunnum, R.,R., et al.., "Analogs of Ceramide That Inhibit Glucocerebroside Synthetase in Mouse Brain," *Chemistry and Physics of Lipids*, LD. Bergelson, et al., eds. (Elsevier/North-Holland Scientific Publishers Ltd.), 26: 265-278 (1980).

Wermuth, C.G., et al.., "Designing Prodrug and Bioprecursors I: Carrier Prodrug", *The Practice of Medicinal Chemistry*, C.G., Wermuth, ed.(CA: Academic Press Limited), pp. 671-696 (1996).

Wong, C-H., et al.., "Synthesis and Evaluation of Homoazasugars as Glycosidase Inhibitors," *J. Org. Chem.*, 60: 1492-1501, (1995).

* cited by examiner

METHODS OF TREATING DIABETES MELLITUS

This application claims priority to U.S. Provisional Application No. 60/626,448, filed on Nov. 10, 2004, which is herein incorporated by reference in its entirety.

FIELD OF THE INVENTION

The invention relates generally to the field of diabetes mellitus. In specific embodiments the invention provides methods of treating a subject suffering from diabetes mellitus.

BACKGROUND OF THE INVENTION

Diabetes mellitus (hereinafter "diabetes") presents a growing worldwide health problem. It is estimated that more than 135 million people suffer from the disease. Type 2 diabetes, also known as non-insulin-dependent diabetes (NIDD) or adult-onset diabetes, accounts for approximately 90-95% of these cases. It is expected that this number will increase 4-5% annually. Serious health problems associated with diabetes include blindness, renal disease, neuropathy, amputation, cardio-vascular disease, stroke and increased risk of mortality. The cost of treating diabetics in the United States alone is estimated be approximately $132 billion per year. Limited resources present a challenge to clinicians to provide comprehensive care to diabetic patients (Florence et al., *American Family Physician* 59(10):2835 (1999)). Thus, there is a significant need for more effective treatment of diabetes.

Type 2 diabetes is linked to obesity, and is characterized by insulin resistance or an inability to respond properly to one's own insulin. In non-diabetic subjects, insulin promotes cellular uptake of glucose from the blood, thereby lowering blood sugar levels while, at the same time, promoting anabolic reactions such as the cellular synthesis of glycogen, fatty acids and proteins (Stryer, 1981, *Biochemistry*, W.H. Freeman and Company, San Francisco).

Resistance to the metabolic actions of insulin is a hallmark of type 2 diabetes. Insulin resistance is characterized by impaired uptake and utilization of glucose in insulin sensitive target organs such as adipocytes and skeletal muscle, and impaired inhibition of hepatic glucose output. The functional insulin deficiency and the failure of insulin to suppress hepatic glucose output results in fasting hyperglycemia. Pancreatic β-cells compensate, at first, for the insulin resistance by secreting increased levels of insulin. However, the β-cells are unable to maintain the high output of insulin and eventually the glucose-induced insulin secretion falls, leading to the deterioration of glucose homeostasis and to subsequent development of overt diabetes.

While the exact cause of type 2 diabetes remains unknown, in vitro results suggest that the interruption of the insulin induced signaling cascade may be associated with elevated levels of the ganglioside GM3. It has also been suggested that the cytokine tumor necrosis factor-α (TNF-α), implicated in insulin resistance, results in increased expression of GM3 (Tagami et al., *J. Biol. Chem.* 277(5):3085 (2002)). Intriguingly, mutant mice lacking GM3 synthase, and thus lacking in GM3, are protected from insulin resistance caused by a high-fat diet (Yamashita et al., *Proc. Natl. Acad. Sci. USA* 100: 3445-3449 (2003)).

Gangliosides such as GM3 are sphingolipids comprised of ceramide and at least one acidic sugar. Gangliosides are generally found in the outer leaflet of the plasma membrane (Nojri et al., *Proc. Natl. Acad. Sci. USA* 83:782 (1986)). They are involved in cell signaling and act as modulators of receptor activity (Yamashita et al., *Proc. Natl. Acad. Sci. USA* 100(6):3445 (2003)).

GM3 consists of a ceramide molecule linked to a trisaccharide consisting of glucose linked to galactose which in turn is linked to the acidic sugar N-acetylneuraminate. GM3 is synthesized in the cell by the enzymatic step-wise addition of activated sugar molecules to a ceramide molecule. The first step in the biosynthesis of GM3 is the addition of glucose to ceramide to form glucosylceramide. This step is catalyzed by the enzyme glucosylceramide synthase. In the second step, a galactose moiety is added to form lactosylceramide, followed by the addition of sialic acid to the terminal galactose residue of lactosylceramide to form GM3.

Regulation of GM3 levels, e.g., by the inhibition of glucosylceramide synthase, has been proposed as a method of treating Gaucher's disease (see, e.g., U.S. Pat. No. 6,569,889). Two types of glucosylceramide synthase inhibitors have been described for treating lysosomal storage diseases such as Gaucher's disease. Both are enzyme substrate analogs which bind to the enzyme active site and prevent substrate binding. The first type of inhibitors are ceramide analogs (see, e.g., U.S. Pat. Nos. 6,569,889; 6,255,336; 5,916,911; 5,302, 609; Lee et al., *J. Biol. Chem.* 274(21):14662 (1999)). The second type of inhibitors are sugar analogs (see, e.g., U.S. Pat. Nos. 6,660,749; 6,610,703; 5,472,969; 5,525,616; Overkleef et al., *J. Biol. Chem.* 273(41):26522 (1998)).

The instant invention provides methods for treating diabetes with inhibitors of glycosphingolipid synthesis as therapeutic agents for diabetes.

SUMMARY OF THE INVENTION

In certain embodiments, the invention provides a method of treating a subject having diabetes, e.g., type 2 diabetes, comprising administering to the subject a therapeutically effective amount of at least one compound that inhibits glycosphingolipid synthesis, e.g., GM3 synthesis, thereby treating the diabetes.

In certain other embodiments, the invention provides a method of treating a subject having diabetes, e.g., type 2 diabetes, comprising administering to the subject a therapeutically effective amount of at least one compound which inhibits glucosylceramide synthase, thereby treating the diabetes. In certain specific embodiments, the glucosylceramide synthase inhibitor is a ceramide analog.

Other embodiments of the invention provide methods of lowering blood glucose in a subject comprising administering to the subject at least one compound which inhibits glycosphingolipid synthesis, e.g., GM3 synthesis, thereby lowering blood glucose levels in the subject. Yet other embodiments of the invention provide methods of lowering blood glucose in a subject comprising administering to the subject at least one compound which inhibits glucosylceramide synthase, thereby lowering blood glucose levels in the subject. In certain specific embodiments, the glucosylceramide synthase inhibitor is a ceramide analog.

In yet other embodiments, the invention provides methods of improving glucose tolerance in a subject comprising administering to the subject at least one compound which inhibits glycosphingolipid synthesis, e.g., GM3 synthesis, thereby improving glucose tolerance in a subject. Yet other embodiments of the invention provide methods of improving glucose tolerance in a subject comprising administering to the subject at least one compound which inhibits glucosylceramide synthase, thereby improving glucose tolerance in the subject. In certain specific embodiments, the glucosylceramide synthase inhibitor is a ceramide analog.

Other embodiments of the invention provide methods of decreasing plasma TNF-α levels in a subject comprising administering to the subject at least one compound which inhibits glycosphingolipid synthesis, e.g., GM3, thereby decreasing TNF-α levels in the subject. Yet other embodiments of the invention provide methods of decreasing plasma TNF-α levels in a subject comprising administering to the subject at least one compound which inhibits glucosylceramide synthase, thereby decreasing plasma TNF-α levels in the subject. In certain specific embodiments, the glucosylceramide synthase inhibitor is a ceramide analog.

Still other embodiments of the invention provide methods of decreasing glycated hemoglobin levels in a subject comprising administering to the subject at least one compound which inhibits glycosphingolipid synthesis, e.g., GM3 synthesis, thereby decreasing glycated hemoglobin levels in the subject. Yet other embodiments of the invention provide methods of decreasing plasma glycated hemoglobin levels in a subject comprising administering to the subject at least one compound which inhibits glucosylceramide synthase, thereby decreasing plasma glycated hemoglobin levels in the subject. In certain specific embodiments, the glucosylceramide synthase inhibitor is a ceramide analog.

In yet other embodiments, the invention provides methods of increasing insulin sensitivity in a subject comprising administering to the subject at least one compound which inhibits glycosphingolipid synthesis, e.g., GM3 synthesis, thereby increasing insulin sensitivity in the subject compared to a subject who has not received the compound. Yet other embodiments of the invention provide methods of increasing insulin sensitivity levels in a subject comprising administering to the subject at least one compound which inhibits glucosylceramide synthase, thereby increasing insulin sensitivity in the subject. In certain specific embodiments, the glucosylceramide synthase inhibitor is a ceramide analog.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 2a shows naïve (unstimulated) 3T3-L1 cells stained for GM3 expression. FIG. 2b shows naïve 3T3-L1 cells stained for GM3 expression after treatment with a glucosylceramide synthase inhibitor. FIG. 2c shows 3T3-L1 cells stained for GM3 expression after stimulation with TNF-α. FIG. 2d shows 3T3-L1 cells stained for GM3 expression after stimulation with TNF-α and treatment with a glucosylceramide synthase inhibitor. The lower panel is the same field as its respective upper panel counter part, but counter stained with 4',6-diamidino-2-phenylindole (DAPI) as a control for cell number.

FIG. 5a is a graph showing the liver weight as percentage of body weight in 3 groups of rats: ZDF rats treated with a glucosylceramide synthase inhibitor (i.e., drug); ZDF rats given water instead of drug; and lean rats given water.

FIG. 5b is a graph showing the kidney weight as percentage of body weight in the same 3 groups of rats described in FIG. 5a.

FIG. 6a is a graph showing blood glucose levels over time for three groups of rats: ZDF rats treated with a glucosylceramide synthase inhibitor (i.e., drug); ZDF rats given water instead of drug; and lean rats given water.

FIG. 6b is a graph showing insulin levels over time for the same three groups of rats described in FIG. 6a.

FIG. 7a shows the results in rats before commencing any drug therapy. FIGS. 7b, 7c, and 7d show the results after 2, 4, and 6 weeks of drug therapy, respectively.

FIG. 10a shows average body weight. FIG. 10b shows average blood glucose levels. FIG. 10c shows average insulin blood levels.

FIG. 11a is a graph showing body weight over time in 3 groups of mice: DIO mice treated with a glucosylceramide synthase inhibitor (i.e., drug); DIO mice given water instead of drug; and lean mice given water.

FIG. 11b is graph showing food intake over time in the same 3 groups of mice described in FIG. 11a.

FIGS. 15a, 15b, and 15c show the results after 4.5, 7.5, and 9.5 weeks of drug therapy, respectively.

DESCRIPTION OF THE EMBODIMENTS

Figure 1:
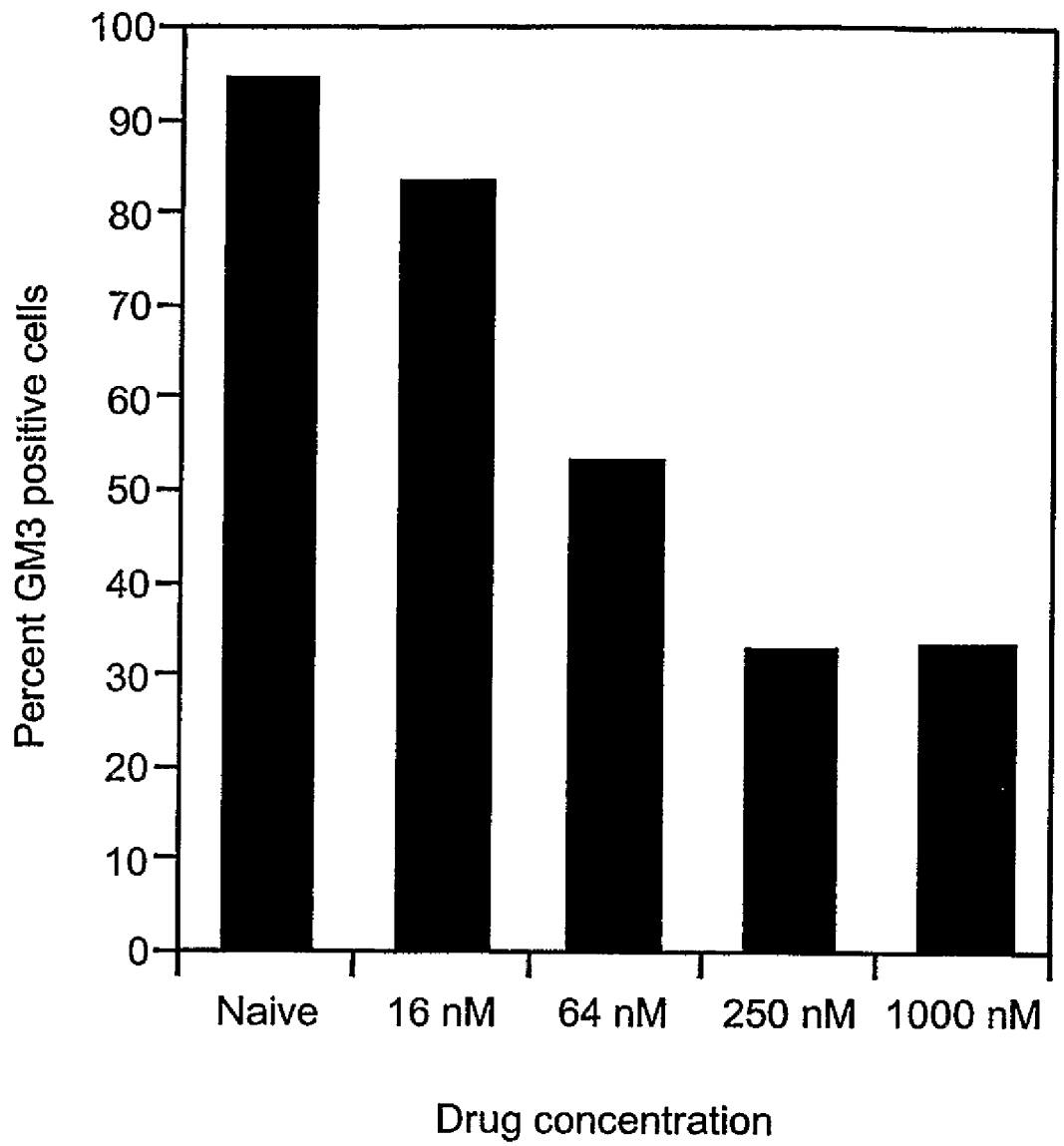
FIG. 1 is a graph showing the percentage of 3T3-L1 cells expressing GM3 in response to increasing concentrations of a glucosylceramide synthase inhibitor.

The invention is based in part on the discovery that inhibitors of glycosphingolipid synthesis, e.g., GM3 synthesis, such as glucosylceramide synthase inhibitors can be used to treat diabetes, e.g., type 2 diabetes.

A. Glycosphingolipid Synthesis Inhibitors

Compounds which inhibit glycosphingolipid synthesis, e.g., GM3 synthesis, are contemplated as therapeutics to treat diabetes, e.g., type 2 diabetes. In specific embodiments, the compound inhibits the enzyme glucosylceramide synthase. As an example, the compound may be an analog of a substrate or a portion of a substrate of glucosylceramide synthase, e.g., a ceramide analog. Suitable ceramide analogs include those described in U.S. Pat. Nos. 6,569,889; 6,255,366; 6,051,598, 5,916,911; Inokuchi et al., *J. Lipid Res.* 28:565 (1987); Shayman et al., *J. Biol. Chem.* 266:22968 (1991); and Bell et al. Ed., 1993, *Advances in Lipid Research: Sphingolipids in Signaling* (Academic Press, San Diego).

In some embodiments, the invention provides an inhibitor of glucosylceramide synthase comprising Formula Ia set forth below:

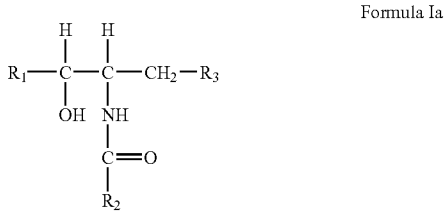

Formula Ia

In certain embodiments, $R_1$ is an aromatic ring, e.g., a phenyl group. The phenyl group may be substituted or unsubstituted. Examples of suitable substituents include, but are not limited to, hydrogen, alkyl, alkenyl, alkenoxy, alkynyl, aldehyde, alkanoyl, alkoxy, amido, amino, aryl, aryloxy, carbonyl-containing group, carboxy, cyano, cycloalkyl, ether, ester, halogen, heterocyclyl, hydroxy, ketone, nitro, oxo, perfluoroalkyl, sulfonyl, sulfonate, and thio groups. The substituent may be joined to form a cycloalkyl or heterocyclyl ring, e.g., a dioxane, including methylenedioxy, ethylenedioxy and propylenedioxy. Where the substituent is an alkyl or alkenyl chain, the chain may be a $C_2$ to $C_{20}$ carbon chain, such as a $C_2$-$C_{12}$ carbon chain or a $C_2$-$C_6$ carbon chain. The alkyl or alkenyl chain may be comprised of a straight or a branched carbon chain. In one embodiment, the alkenyl chain may have a double bond on the carbon atom bonded to the —C(H)(OH)— unit of Formula Ia. The aliphatic chain may have a hydroxyl group, e.g., positioned one or two carbon atoms away from the two asymmetric centers of Formula Ia.

In certain embodiments, $R_2$ is an alkyl, alkenyl, or alkynyl chain e.g., a $C_2$ to $C_{20}$ carbon chain. In some embodiments, the alkyl, alkenyl, or alkynyl chain is a $C_6$ to $C_{10}$ carbon chain. In some embodiments, the alkyl, alkenyl, or alkynyl chain is a $C_7$ to $C_{18}$ carbon chain. In specific embodiments, the alkyl, alkenyl, or alkynyl chain is a $C_7$ chain. In other specific embodiments, the alkyl, alkenyl, or alkynyl chain is a $C_8$ chain. In certain embodiments, the alkyl chain may be optionally substituted with a hydroxyl group.

In certain embodiments, $R_3$ is an amine group, e.g., a tertiary amine. In some embodiments, the amine group is a cyclic amine, e.g., pyrrolidine, azetidine, piperidine. In some specific embodiments the amine group is not a morpholine group.

In some embodiments the nitrogen atom of the amine group of $R_3$ is attached to the —$CH_2$ group of Formula Ia. In these embodiment $R_3$ may have the structure shown in Formula II below:

Formula II $R_{18}$ and $R_{19}$ may each be independently selected from hydrogen, alkyl, alkenyl, alkynyl, alkoxy, aryl, arylalkyl, carbonyl-containing group, carboxy, cyano, cycloalkyl, ester, ether, heterocyclyl, hydroxy, ketone, nitro, sulfonyl, and thio.

Alternatively, $R_{18}$ and $R_{19}$ may be taken together with N to form a heterocyclyl group bonded to at least one substituent independently selected from hydrogen, alkyl, alkenyl, alkenoxy, alkynyl, aldehyde, alkanoyl, alkoxy, amido, amino, aryl, aryloxy, carbonyl-containing group, carboxy, cyano, cycloalkyl, ether, ester, halogen, heterocyclyl, hydroxy, ketone, nitro, oxo, perfluoroalkyl, sulfonyl, sulfonate, and thio.

The compounds of Formula Ia may be present in the form of their racemates, racemic mixtures, pure enantiomers, diastereomers, and mixtures thereof. All four configurational isomers of the compounds described above (e.g., D-threo, L-threo, D-erythro, L-erythro) are contemplated within the present invention, and may be used either singly or in combination.

In a specific embodiment the glucosylceramide synthase inhibitor is 1-(3',4'-ethylenedioxy)phenyl-2-nonanoylamino-3-pyrrolidino-1-propanol. In another embodiment the glucosylceramide synthase inhibitor is 1-(3',4'-ethylenedioxy)phenyl-2-octanoylamino-3-pyrrolidino-1-propanol.

The invention further provides an inhibitor of glucosylceramide synthase comprising Formula Ib set forth below:

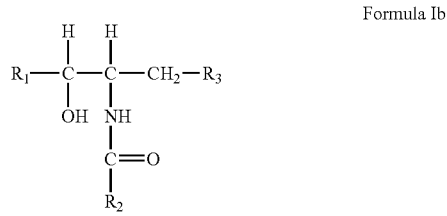

Formula Ib

In certain embodiments, $R_1$ is an optionally substituted aromatic ring or an optionally substituted heterocycle. The aromatic or heterocyclic ring may be substituted or unsubstituted. Examples of suitable substituents include, but are not limited to, hydrogen, alkyl, alkenyl, alkenoxy, alkynyl, aldehyde, alkanoyl, alkoxy, amido, amino, aryl, aryloxy, carbonyl-containing group, carboxy, cyano, cycloalkyl, ether, ester, halogen, heterocyclyl, hydroxy, ketone, nitro, oxo, perfluoroalkyl, sulfonyl, sulfonate, and thio groups. The substituent may be joined to form a cycloalkyl or heterocyclyl ring, e.g., a dioxane, including methylenedioxy, ethylenedioxy and propylenedioxy. Where the substituent is an alkyl or alkenyl chain, the chain may be a $C_2$ to $C_{20}$ carbon chain, such as a $C_2$-$C_{12}$ carbon chain or a $C_2$-$C_6$ carbon chain. The alkyl or alkenyl chain may be comprised of a straight or a branched carbon chain. In one embodiment, the alkenyl chain may have a double bond on the carbon atom bonded to the —C(H)(OH)— unit of Formula Ib. The aliphatic chain may have a hydroxyl group, e.g., positioned one or two carbon atoms away from the two asymmetric centers of Formula Ib.

In certain embodiments, $R_1$ is substituted phenyl, such as, e.g., phenyl substituted with hydroxy, methoxy, chloro, or fluoro. For example, $R_1$ may be 3,4-methylenedioxyphenyl, 3,4-ethylenedioxyphenyl, 3,4-propylenedioxyphenyl, 2-hydroxyphenyl, 3-hydroxyphenyl, 4-hydroxyphenyl, 2-methoxyphenyl, 3-methoxyphenyl, 4-methoxyphenyl, 3,4-dimethoxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, or 4-iodophenyl.

In certain embodiments, $R_2$ is an optionally substituted alkyl, alkenyl, or alkynyl chain e.g., a $C_2$ to $C_{20}$ carbon chain. In some embodiments, the alkyl, alkenyl, or alkynyl chain is a $C_6$ to $C_{10}$ carbon chain. In some embodiments, the alkyl, alkenyl, or alkynyl chain is a $C_7$ to $C_{18}$ carbon chain. In specific embodiments, the alkyl, alkenyl, or alkynyl chain is a $C_7$ chain. In other specific embodiments, the alkyl, alkenyl, or alkynyl chain is a $C_8$ chain. In certain embodiments, the alkyl chain may be optionally substituted with a hydroxyl group.

In particular embodiments, $R_2$ is an alkyl, alkenyl, or alkynyl chain substituted with at least one substituent independently selected from hydrogen, alkyl, alkenyl, alkenoxy, alkynyl, aldehyde, alkanoyl, alkoxy, amido, amino, aryl, aryloxy, carbonyl-containing group, carboxy, cyano, cycloalkyl, ether, ester, halogen, heterocyclyl, hydroxy, ketone, nitro, oxo, perfluoroalkyl, sulfonyl, sulfonate, and thio. In embodiments wherein $R_2$ is a 1-heptyl chain, the 1-heptyl chain may be optionally substituted at, e.g., position 1 and/or 6, and in embodiments wherein $R_2$ is a 1-octyl chain, the 1-octyl chain may be optionally substituted at, e.g., position 1 and/or 7. For example, $R_2$ may be 1-(1-hydroxyheptyl) (Formula III), 1-(6-hydroxyheptyl) (Formula IV), 1-(1-hydroxyoctyl) (Formula V), or 1-(7-hydroxyoctyl) (Formula VI).

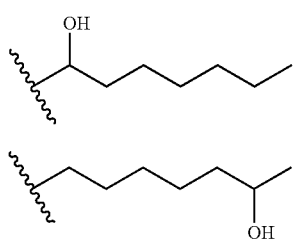

Formula III

Formula IV

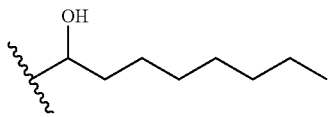

Formula V

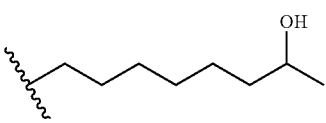

Formula VI

In certain embodiments, $R_3$ is an optionally substituted amine group, e.g., a tertiary amine. In some embodiments, the amine group is a cyclic amine, e.g., pyrrolidine, azetidine, piperidine. In other embodiments, $R_3$ is a cyclic amine such as, e.g., piperazine, morpholine, or hexamethyleneimine. In some specific embodiments the amine group is not a morpholine group. For example, in embodiments wherein $R_1$ is unsubstituted phenyl and $R_2$ is n-nonyl, $R_3$ is not a morpholine group.

In some embodiments the nitrogen atom of the amine group of $R_3$ is attached to carbon 3 of the 2-amino-1-propanol backbone of Formula Ib (to the —CH$_2$— group). In these embodiment $R_3$ may have the structure shown in Formula II below:

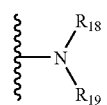

Formula II $R_{18}$ and $R_{19}$ may each be independently selected from hydrogen, alkyl, alkenyl, alkynyl, alkoxy, aryl, arylalkyl, carbonyl-containing group, carboxy, cyano, cycloalkyl, ester, ether, heterocyclyl, hydroxy, ketone, nitro, sulfonyl, and thio.

Alternatively, $R_{18}$ and $R_{19}$ may be taken together with N to form a heterocyclyl group bonded to at least one substituent independently selected from hydrogen, alkyl, alkenyl, alkenoxy, alkynyl, aldehyde, alkanoyl, alkoxy, amido, amino, aryl, aryloxy, carbonyl-containing group, carboxy, cyano, cycloalkyl, ether, ester, halogen, heterocyclyl, hydroxy, ketone, nitro, oxo, perfluoroalkyl, sulfonyl, sulfonate, and thio.

The compounds of Formula Ib may be present in the form of their racemates, racemic mixtures, pure enantiomers, diastereomers, and mixtures thereof. The chirality at any chiral center may be either R or S. For example, with regard to positions 1 and 2 and of the 2-amino-1-propanol framework of Formula Ib, all four configurational isomers (e.g., D-threo, L-threo, D-erythro, L-erythro) are contemplated within the present invention, and may be used either singly or in combination.

In a specific embodiment the glucosylceramide synthase inhibitor is 1-(3',4'-ethylenedioxy)phenyl-2-nonanoylamino-3-pyrrolidino-1-propanol (Formula VII).

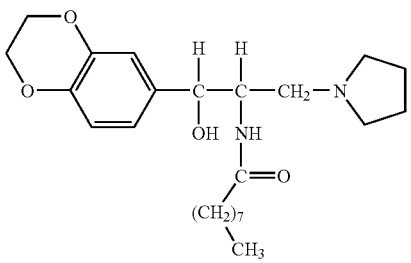

Formula VII

For example, the glucosylceramide synthase inhibitor may be 1(R)-(3',4'-ethylenedioxy)phenyl-2(R)-nonanoylamino-3-pyrrolidino-1-propanol. In another embodiment the glucosylceramide synthase inhibitor is 1-(3',4'-ethylenedioxy)phenyl-2-octanoylamino-3-pyrrolidino-1-propanol (Formula VIII).

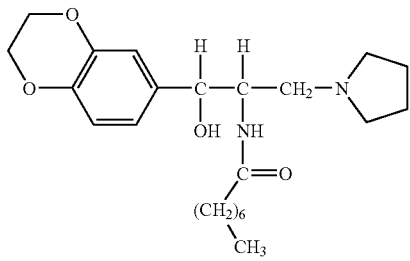

Formula VIII

For example, the glucosylceramide synthase inhibitor may be 1(R)-(3',4'-ethylenedioxy)phenyl-2(R)-octanoylamino-3-pyrrolidino-1-propanol.

The compounds of Formula Ia or Formula Ib may be administered as a prodrug. The compounds of Formula Ia or Formula Ib may be provided in free base form or as a pharmaceutically acceptable salt. Pharmaceutically acceptable salts are described in more detail below.

Methods of making the glucosylceramide synthase inhibitors set forth above have been described in, e.g., U.S. Pat. Nos. 6,569,889; 6,255,336; 5,916,911; 5,302,609; Lee et al., J. Biol. Chem. 274(21) (1999):14662; Abe et al., J. Biochem. 111:191 (1992); Inokuchi et al., J. Lipid Res. 28:565 (1987).

The term "alkanoyl," as used herein, refers to a carbonyl group attached to an alkyl group.

The term "alkanoyloxy," as used herein, refers to an alkanoyl group attached to an oxygen, e.g., —C(O)-alkyl-O—.

The term "alkenyl," as used herein, refers to an unsaturated straight or branched chain of 2-20 carbon atoms having at least one carbon-carbon double bond, such as a straight or branched chain group of 2-12, 2-10, or 2-6 carbon atoms.

The term "alkoxy," as used herein, refers to an alkyl group attached to an oxygen. "Alkoxy" groups can optionally contain alkenyl ("alkenoxy") or alkynyl ("alkynoxy") groups.

The term "alkyl," as used herein, refers to a saturated straight or branched chain group of 1-20 carbon atoms, such as a straight or branched chain group of 1-12, 1-10, or 1-8 carbon atoms.

"Alkyl," "alkenyl," and "alkynyl" groups, collectively referred to as "saturated and unsaturated hydrocarbons," can be optionally substituted with, or interrupted by, at least one group selected from aldehyde, alkoxy, amido, amino, aryl, carboxy, cyano, cycloalkyl, ester, ether, halogen, heterocyclyl, hydroxy, ketone, nitro, sulfonate, sulfonyl, thio, O, S, and N.

The term "alkynyl," as used herein, refers to an unsaturated straight or branched chain group of 2-20 carbon atoms having at least one carbon-carbon triple bond, such as a straight or branched chain group of 2-12, 2-10, or 2-6 carbon atoms.

The term "amido," as used herein, refers to a radical of the form —$R_5C(O)N(R_6)$—, —$R_5C(O)N(R_6)R_7$—, or —$C(O)NR_6R_7$, where $R_5$, $R_6$ and $R_7$ are each independently selected from hydrogen, alkyl, alkanoyl, alkenyl, alkoxy, alkynyl, aryl, carboxy, cycloalkyl, ester, ether, heterocyclyl, hydroxy, ketone, thio, and sulfonyl, and $R_5$ is selected from hydrogen, alkyl, alkoxy, amido, amino, aryl, cycloalkyl, ester, ether, heterocyclyl, halogen, hydroxy, ketone, and thio. The amido may be attached to another group through the carbon, the nitrogen, $R_5$, $R_6$, or $R_7$. The amido also may be cyclic, for example $R_6$ and $R_7$, $R_5$ and $R_6$, or $R_5$ and $R_7$ may be joined to form a 3- to 12-membered ring, such as a 3- to 10-membered ring. The term "amido" encompasses groups such as alkanoylaminoalkyl, amidoalkyl (attached to the parent molecular group through the alkyl), alkylamido (attached to the parent molecular group through the amido), arylamido, amidoaryl, sulfonamide, etc. The term "amido" also encompasses groups such as urea, carbamate, and cyclic versions thereof.

The term "amino," as used herein, refers to a radical of the form —$NR_8R_9$, —$N(R_8)R_9$—, or —$R_9N(R_8)R_{10}$— where $R_8$, $R_9$, and $R_{10}$ are independently selected from hydrogen, alkyl, alkenyl, alkanoyl, alkoxy, alkynyl, amido, amino, aryl, carboxy, cycloalkyl, ester, ether, heterocyclyl, hydroxy, ketone, thio, and sulfonyl. The amino may be attached to the parent molecular group through the nitrogen, $R_8$, $R_9$, or $R_{10}$. The amino also may be cyclic, for example any two of $R_8$, $R_9$, and $R_{10}$ may be joined together, or with the N, to form a 3- to 12-membered ring, e.g., morpholino or piperidinyl. The term "amino" encompasses groups such as aminoalkyl (attached to the parent molecular group through the alkyl), alkylamino (attached to the parent molecular group through the amino), arylamino, aminoaryl, sulfonamino, etc. The term "amino" also includes the corresponding quaternary ammonium salt of any amino group, e.g., —$[N(R_8)(R_9)(R_{10})]^+$.

The term "aryl," as used herein, refers to a mono-, bi-, or other multi-carbocyclic, aromatic ring system. The aryl group may optionally be fused to one or more rings selected from aryls, cycloalkyls, and heterocyclyls. The aryl group may be optionally substituted with groups selected from alkyl, aldehyde, alkanoyl, alkoxy, amino, amido, aryl, carboxy, cyano, cycloalkyl, ester, ether, halogen, heterocyclyl, hydroxy, ketone, nitro, sulfonate, sulfonyl, and thio.

The term "aryloxy," as used herein, refers to an aryl group attached to an oxygen atom.

The term "carbonyl," as used herein, refers to the radical —C(O)—.

The term "carboxy," as used herein, refers to the radical —COOH. The term "carboxy" also includes salts such as —COONa, etc.

The term "cyano," as used herein, refers to the radical —CN.

The term "cycloalkoxy," as used herein, refers to a cycloalkyl group attached to an oxygen, e.g., —O-cycloalkyl-.

The terms "disease or condition," as used herein, refers to diabetes mellitus.

The term "ester," as used herein, refers to a radical having the structure —C(O)O—, —C(O)O—$R_{11}$—, —$R_{12}C(O)O$—$R_{11}$—, or —$R_{12}C(O)O$—, where $R_{11}$ is not hydrogen and O is not bound to hydrogen. $R_{11}$ or $R_{12}$ may be independently selected from an alkyl, alkenyl, alkynyl, aryl, cycloalkyl, ester, ether, heterocyclyl, ketone, and thio. $R_{12}$ may be a hydrogen. The ester may be cyclic, for example the carbon atom and $R_{11}$, the oxygen atom and $R_{12}$, or $R_{11}$ and $R_{12}$ may be joined to form a 3- to 12-membered ring. Exemplary esters include alkoxyalkanoyl, alkoxycarbonyl, alkoxycarbonylalkyl, etc. Esters also include carboxylic acid anhydrides and acid halides.

The term "ether," as used herein, refers to a radical having the structure —$R_{13}$O—$R_{14}$—, where $R_{13}$ and $R_{14}$ are not hydrogen. The ether may be attached to the parent molecular group through $R_{13}$ or $R_{14}$. $R_{13}$ or $R_{14}$ may be independently selected from an alkyl, alkenyl, alkynyl, aryl, cycloalkyl, or heterocyclyl. Exemplary ethers include alkoxyalkyl and alkoxyaryl groups. Ether also includes polyethers, e.g., where one or both of $R_{13}$ and $R_{14}$ are ethers.

The terms "halo," or "halogen," as used herein, refer to F, Cl, Br, or I.

The terms "heterocycle," "heterocyclyl," or "heterocyclic," as used herein, are synonymous and refer to a saturated or unsaturated 3-, 4-, 5-, 6-, or 7-membered ring containing one, two, or three heteroatoms independently selected from nitrogen, oxygen, and sulfur. Heterocycles may be aromatic (heteroaryls) or non-aromatic. Heterocycles may be optionally substituted with one or more substituents including alkyl, alkenyl, alkynyl, aldehyde, alkoxy, amido, amino, aryl, carboxy, cyano, cycloalkyl, ester, ether, halogen, heterocyclyl, hydroxy, ketone, oxo, nitro, sulfonate, sulfonyl, and thio.

Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

Heterocycles also include bridged bicyclic groups where a monocyclic heterocyclic group may be bridged by an alkylene group such as

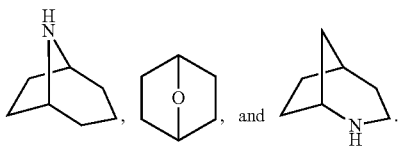

Heterocycles also include compounds of the formula

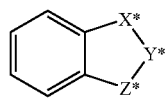

where X* and Z* are independently selected from —$CH_2$—, —$CH_2NH$—, —$CH_2O$—, —NH— and —O—, with the proviso that at least one of X* and Z* is not —$CH_2$—, and Y* is selected from —C(O)— and —$(C(R'')_2)_v$—, where R" is a hydrogen or $C_{1-4}$ alkyl, and v is an integer of 1-3, inclusive. These heterocycles include 1,3-benzodioxolyl, 1,4-benzodioxanyl, and 1,3-benzimidazol-2-one.

The terms "hydroxy" and "hydroxyl," as used herein, refer to the radical —OH.

"Glucose tolerance," as used herein, refers to the ability of a subject to maintain glucose homeostasis, after administration of glucose, or some other sugar that may be converted to glucose, or after consumption of a food item either containing glucose or that may, after consumption, be converted to glucose. Glucose homeostasis may be maintained by cellular uptake of glucose to maintain blood glucose levels within a physiologically acceptable range.

"Insulin sensitivity," as used herein, refers to the ability of insulin to stimulate cells to take up glucose.

The term "ketone," as used herein, refers to a radical having the structure —$R_{15}$—C(O)—$R_{16}$—. The ketone may be attached to another group through $R_{15}$ or $R_{16}$. $R_{15}$ or $R_{16}$ may be independently alkyl, alkenyl, alkynyl, cycloalkyl, heterocyclyl or aryl. Alternatively, $R_{15}$ or $R_{16}$ may be joined to form a 3- to 12-membered ring. Exemplary ketones include alkanoylalkyl, alkylalkanoyl, etc.

The term "nitro," as used herein, refers to the radical —$NO_2$.

The term "oxo," as used herein, refers to an oxygen atom with a double bond to another atom. For example, a carbonyl is a carbon atom with an oxo group.

The term "perfluoroalkyl," as used herein, refers to an alkyl group in which all of the hydrogen atoms have been replaced by fluorine atoms.

The term "phenyl," as used herein, refers to a monocyclic carbocyclic ring system having one aromatic ring. The phenyl group may also be fused to a cyclohexane or cyclopentane ring. The phenyl groups may be optionally substituted with one or more substituents including alkyl, alkenyl, alkynyl, aldehyde, alkoxy, amido, amino, aryl, carboxy, cyano, cycloalkyl, ester, ether, halogen, heterocyclyl, hydroxy, ketone, nitro, sulfonate, sulfonyl, and thio.

"Pharmaceutically acceptable excipient," as used herein, refers to any and all solvents, dispersion media, coatings, antibacterial and antifungal agents, isotonic and absorption delaying agents, and the like, that are compatible with pharmaceutical administration.

The term "prodrug," as used herein, represents compounds that are rapidly transformed in vivo to a compound of the formulas described herein, for example, by hydrolysis in the blood. A discussion is provided in Han *AAPS Pharmsci* 2(1):6 (2000), and in Roche, ed., 1987, *Bioreversible Carriers in Drug Design*, American Pharmaceutical Association and Pergamon Press.

"Subject," as used herein, refers to any mammal, including, but not limited to, humans.

The term "thio," as used herein, refers to a radical having the structure $R_{17}$S—, where $R_{17}$ may be selected from hydrogen, alkyl, aryl, cycloalkyl, heterocyclyl, amino, and amido, e.g., alkylthio, arylthio, thiol, etc. "Thio" may also refer to a radical where the oxygen is replaced by a sulfur, e.g., —N—C (S)— is thioamide or aminothiocarbonyl, alkyl-S— is thioalkoxy (synonymous with alkylthio).

"Treat," "treatment," and "treating," as used herein, refer to any of the following: the reduction in severity of a disease or condition; the reduction in the duration of a disease course; the amelioration of one or more symptoms associated with a disease or condition; the provision of beneficial effects to a subject with a disease or condition, without necessarily curing the disease or condition; the prophylaxis of one or more symptoms associated with a disease or condition. As used herein, the terms "treat," "treatment," and "treating" do not include the treatment of renal hypertrophy and hyperplasia associated with diabetic nephropathy, unless explicitly stated otherwise.

B. Pharmaceutical Compositions

Pharmaceutical compositions for use in the methods of the invention are provided. The compositions of the invention comprise a glucosylceramide synthase inhibitor and a pharmaceutically acceptable carrier or excipient. Examples of suitable pharmaceutical carriers are described in, e.g., E. W. Martin, 1990, *Remington's Pharmaceutical Sciences*, 17th Ed., Mack Pub. Co., Easton, Pa.). Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The compositions of the invention may also contain pH buffering reagents and wetting or emulsifying agents. The compositions may further contain other active compounds providing supplemental, additional, or enhanced therapeutic functions. The pharmaceutical compositions may also be included in a container, pack, or dispenser together with instructions for administration.

Pharmaceutically acceptable salts may be particularly suitable for medical applications because of their greater solubility in water compared with the starting or base compounds. In one embodiment, these salts may have a pharmaceutically acceptable anion or cation. Suitable pharmaceutically acceptable acid addition salts of the compounds of the invention include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Suitable pharmaceutically acceptable basic salts include ammonium salts, alkali metal salts (such as sodium and potassium salts) and alkaline earth metal salts (such as magnesium and calcium salts).

C. Modes of Administration and Dosing

For oral administration, the pharmaceutical compositions of the invention may take the form of tablets or capsules prepared by conventional means. Oral compositions generally include an inert diluent or an edible carrier. They can be enclosed in gelatin capsules or compressed into tablets. For the purpose of oral therapeutic administration, the compounds of Formula Ia or Formula Ib can be incorporated with excipients and used in the form of tablets, or capsules. Pharmaceutically compatible binding agents, and/or adjuvant materials can be included as part of the composition. The tablets, pills, capsules, and the like can contain any of the following ingredients, or compounds of a similar nature; a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The compositions of the invention may also be prepared as a liquid for example a syrup or a suspension. The liquid may include suspending agents (e.g., sorbitol syrup, cellulose derivatives, or hydrogenated edible fats), emulsifying agents (lecithin or acacia), non-aqueous vehicles (e.g., almond oil, oily esters, ethyl alcohol, or fractionated vegetable oils), and preservatives (e.g., methyl- or propyl-p-hydroxybenzoates, or sorbic acid). The preparations may also include flavoring, coloring, and sweetening agents. Alternatively, the composition may be presented as a dry product for constitution with water or other suitable vehicle. For buccal and sublingual administration, the composition may take the form of tablets, lozenges, or fast dissolving films according to conventional protocols.

For administration by inhalation, the compounds for use according to the present invention are conveniently delivered in the form of an aerosol spray from a pressurized pack or nebulizer (e.g., in PBS), with a suitable propellant, e.g., dichlorodifluoromethane, trichlorofluoromethane, dichlorotetrafluoromethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The pharmaceutical compositions of the invention may be formulated for parenteral administration (i.e., intravenous or intramuscular) by bolus injection. Formulations for injection may be presented in unit dosage form, e.g., in ampoules or in multidose containers with an added preservative. The compositions may take such forms as suspensions, solutions, or emulsions in oily or aqueous vehicles, and contain formulatory agents such as suspending, stabilizing, and/or dispersing agents. Alternatively, the active ingredient may be in powder form for constitution with a suitable vehicle, e.g., pyrogen free water.

The pharmaceutical compositions of the invention may also be formulated for rectal administration as a suppository or retention enema, e.g., containing conventional suppository bases such as cocoa butter or other glycerides.

The dose of the GM3 inhibitor generally, and the glucosylceramide synthase inhibitor specifically will vary depending on the subject and upon the particular route of administration used. Dosages may range from 0.1 to 500 mg/kg body weight per day. In one embodiment, the dosing range is 1-20 mg/kg/day. The GM3 inhibitor may be administered continuously or at specific timed intervals. For example, the GM3 inhibitor may be administered 1, 2, 3, or 4 times per day, such as, e.g., a daily or twice-daily formulation. Commercially available assays may be employed to determine optimal dose ranges and/or schedules for administration. Assays for measuring blood glucose levels are commercially available (e.g., OneTouch®Ultra®, Lifescan, Inc. Milpitas, Calif.). Kits to measure human insulin levels are also commercially available (Linco Research, Inc. St. Charles, Mo.).

Additionally, effective doses may be extrapolated from dose-response curves obtained from animal models. The use of diabetic animal models is described infra. Other animal models are known in the art (see, e.g., Comuzzie et al., *Obes. Res.* 11(1):75 (2003); Rubino et al., *Ann. Surg.* 240(2):389 (2004); Gill-Randall et al., *Diabet. Med.* 21(7):759 (2004)). Therapeutically effective dosages achieved in one animal model can be converted for use in another animal, including humans, using conversion factors known in the art (see, e.g., Freireich et al., *Cancer Chemother. Reports* 50(4):219 (1996) and Table 2 below for equivalent surface area dosage factors).

TABLE 2

| To: | From: | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

D. Combination Therapy

The invention also contemplates combination therapies for treating diabetes mellitus. The combination therapy may comprise any of the compounds described herein and at least one other compound suitable for treating diabetes. Examples of compounds used to treat type 2 diabetes include, but are not limited to, insulin (Novolin®, Novolog®; Velosulin®, Novo Nordisk A/S), sulfonylurea (Diabinese®, Glucotrol®, Glucotrol XL®; Pfizer, New York, N.Y.) (Diabeta®, Amaryl®; Aventis, Bridgewater, N.J.), metformin, α-glucosidase inhibitors (Glyset®; Pharmacia, New York, N.Y.), thiazolidinedione (Actos®; Takeda Pharmaceuticals America, Inc, Lincolnshire, Ill.) (Avandia®; GlaxoSmithKline, Upper Merrian, Pa.), glyburide (Orinase®, Tolinase®, Micronase®, Glynase®; Pharmacia Corp., New York, N.Y.) nateglinide (Starlix®; Novartis Pharmaceuticals, Cambridge, Mass.), repaglinide (Prandin®; Novo Nordisk, Princeton, N.J.) and combination drugs such as Avandamet® (GlaxoSmithKline, Upper Merrian, Pa.).

EXAMPLES

Example 1

Inhibition of GM3 in 3T3-L1 Cells

Undifferentiated 3T3-L1 preadipocytes were treated with D-threo-1-(3',4'-ethylenedioxy)phenyl-2-nonanoylamino-3-pyrrolidino-1-propanol at concentrations of 0, 16, 64, 250, and 1000 nM for 48 hours. The cells were harvested and incubated with a 1/100 dilution of a mouse monoclonal anti-GM3 IgM antibody (Seikagaku America, Falmouth, Mass.) followed by a 1/100 dilution of a fluorescently labeled goat anti-mouse IgM (Alexa Fluor 488®) (Molecular Probes, Eugene, Oreg.). The percentage of GM3 positive cells was determined by fluorescent activated cell sorter (FACS) analysis. The results showed that D-threo-1-(3',4'-ethylenedioxy)phenyl-2-nonanoylamino-3-pyrrolidino-1-propanol reduced GM3 levels in a dose dependent manner up to 250 nM (FIG. 1).

Example 2

Inhibition of TNF-α Induced GM3 in Differentiated Adipocytes

Figure 2:
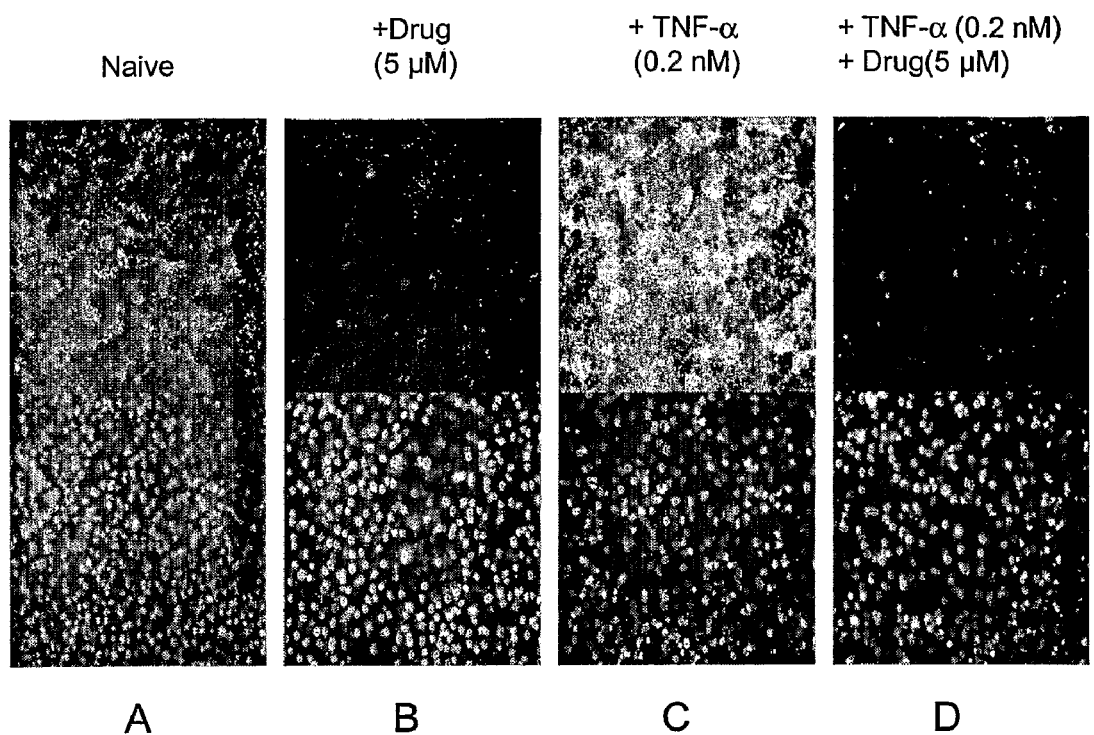
FIG. 2 is a photograph showing immuno-fluorescence of differentiated 3T3-L1 adipocytes. The upper panels shows cells stained for GM3.

3T3-L1 cells were grown to confluence in Dulbeco's Modified Eagle Media (DMEM) (Invitrogen/Gibco, Carlsbad, Calif.) supplemented with 10% calf serum (Invitrogen/Gibco, Carlsbad, Calif.). Differentiation was induced by changing the medium to DMEM supplemented with 10% fetal bovine serum (FBS) (Sigma-Aldrich, St. Louis, Mo.), 0.5 mM 3-isobutyl-1-methylxanthine (Sigma-Aldrich, St. Louis, Mo.), 1 µM dexamethasone (Sigma-Aldrich, St. Louis, Mo.), and 1.7 µM insulin (Sigma-Aldrich, St. Louis, Mo.). After 72 hours, the medium was changed to DMEM supplemented with 10% FBS and 100 ng/ml insulin. Ten days after the induction of differentiation, more than 90% of the cells had differentiated into adipocytes as determined by staining with Oil Red, a histochemical stain for lipid. The adipocytes were then incubated in the presence or absence of 0.2 nM TNF-α, or 5 µM D-threo-1-(3',4'-ethylenedioxy)phenyl-2-nonanoylamino-3-pyrrolidino-1-propanol, or both for 96 hours. The treated cells were then immunostained for GM3 (FIG. 2 upper panels) or counterstained with DAPI (FIG. 2 lower panels). As shown in FIGS. 2c and 2d respectively, 0.2 nM TNF-α induced expression of GM-3 in differentiated adipocytes and 5 µM D-threo-1-(3',4'-ethylenedioxy)phenyl-2-nonanoylamino-3-pyrrolidino-1-propanol abrogated this effect.

Example 3

In Vivo Reduction of Glucosylceramide Levels

Figure 3:
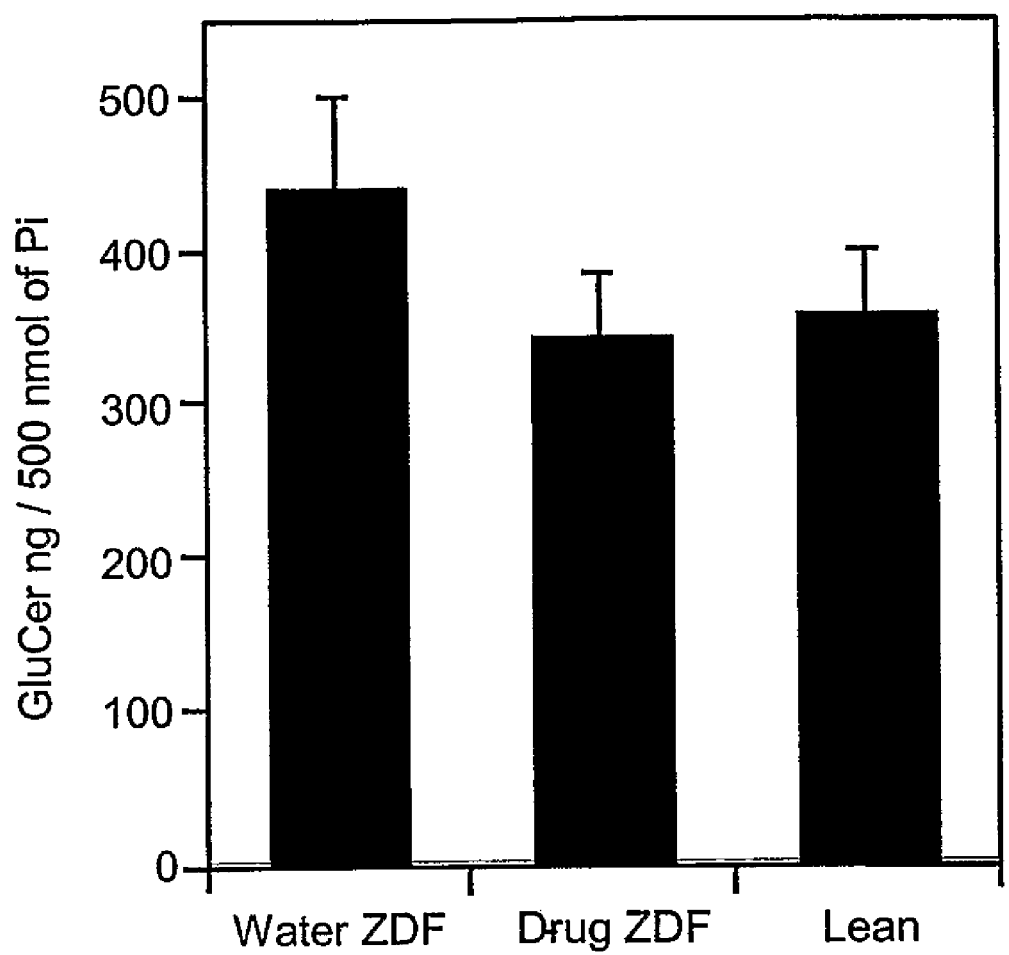
FIG. 3 is a graph comparing glucosylceramide levels in the liver of Zucker Diabetic Fatty (ZDF) rats treated with a glucosylceramide synthase inhibitor or given water instead. Glucosylceramide levels in the liver of lean rats given water is shown as a control.

Zucker Diabetic Fatty (ZDF) fa/fa rats are an accepted animal model for type 2 diabetes (Hunt et al., *Fed. Proc.* 35(5):1206 (1976)). Four week old ZDF rats, as well as lean control littermates, were obtained from Charles River Laboratories (Wilmington, Mass.). The rats were housed at 24° C. with a 12-hour light:dark cycle, and fed with Purina 5008 chow (Purina Mills, LLC, St. Louis Mo.). The rats were acclimatized for one week prior to the study. The rats were then orally gavaged daily with water for 7 days to acclimate them to the oral gavage procedure. After the initial 7 days, they received a daily oral gavage of 75 mg/kg of D-threo-1-(3',4'-ethylenedioxy)phenyl-2-nonanoylamino-3-pyrrolidino-1-propanol for 6 weeks. The control groups, age-matched ZDF rats and lean rats, were orally gavaged daily with water. At the end of the study, livers were harvested, and glucosylceramide (GL1) was extracted and assayed by thin layer chromatography. The levels of GL1 were normalized to equivalents of 500 nmol inorganic phosphates (Pi). (N=6 rats per group±SEM). The results (FIG. 3) showed that rats treated with the drug not only had lower GL1 levels then the non-treated ZDF rats, but also had lower GL1 levels than the non-treated lean rats.

Figure 4:
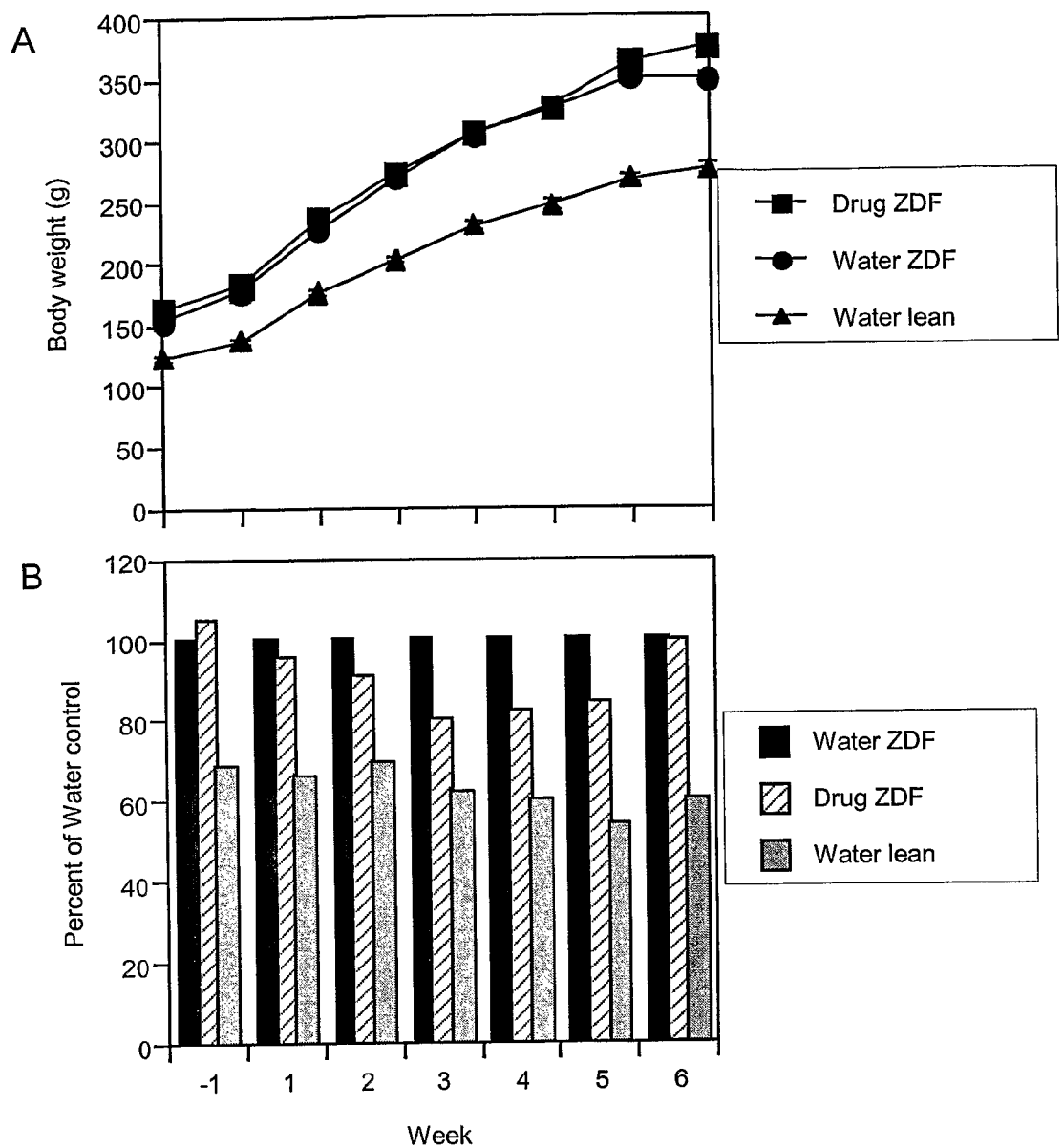
FIG. 4a is a graph showing the average weight over time for three groups of rats: ZDF rats treated with a glucosylceramide synthase inhibitor (i.e., drug); ZDF rats given water instead of drug; and lean rats given water.
FIG. 4b is a graph showing food intake over time in 3 groups of rats as described above for FIG. 4a. The results are presented as a percentage of food intake in ZDF rats given water instead of drug.

Each group of rats were also monitored for several physiological parameters. D-threo-1-(3',4'-ethylenedioxy)phenyl-2-nonanoylamino-3-pyrrolidino-1-propanol did not significantly affect body weight or food consumption in ZDF rats. Body weights and food intake from each group were monitored 2-3 times a week. The average body weights for each group (FIG. 4a) and the percent of food consumed relative to the water treated ZDF control group for each group are shown (FIG. 4b) (N=6 rats per group).

Figure 5:
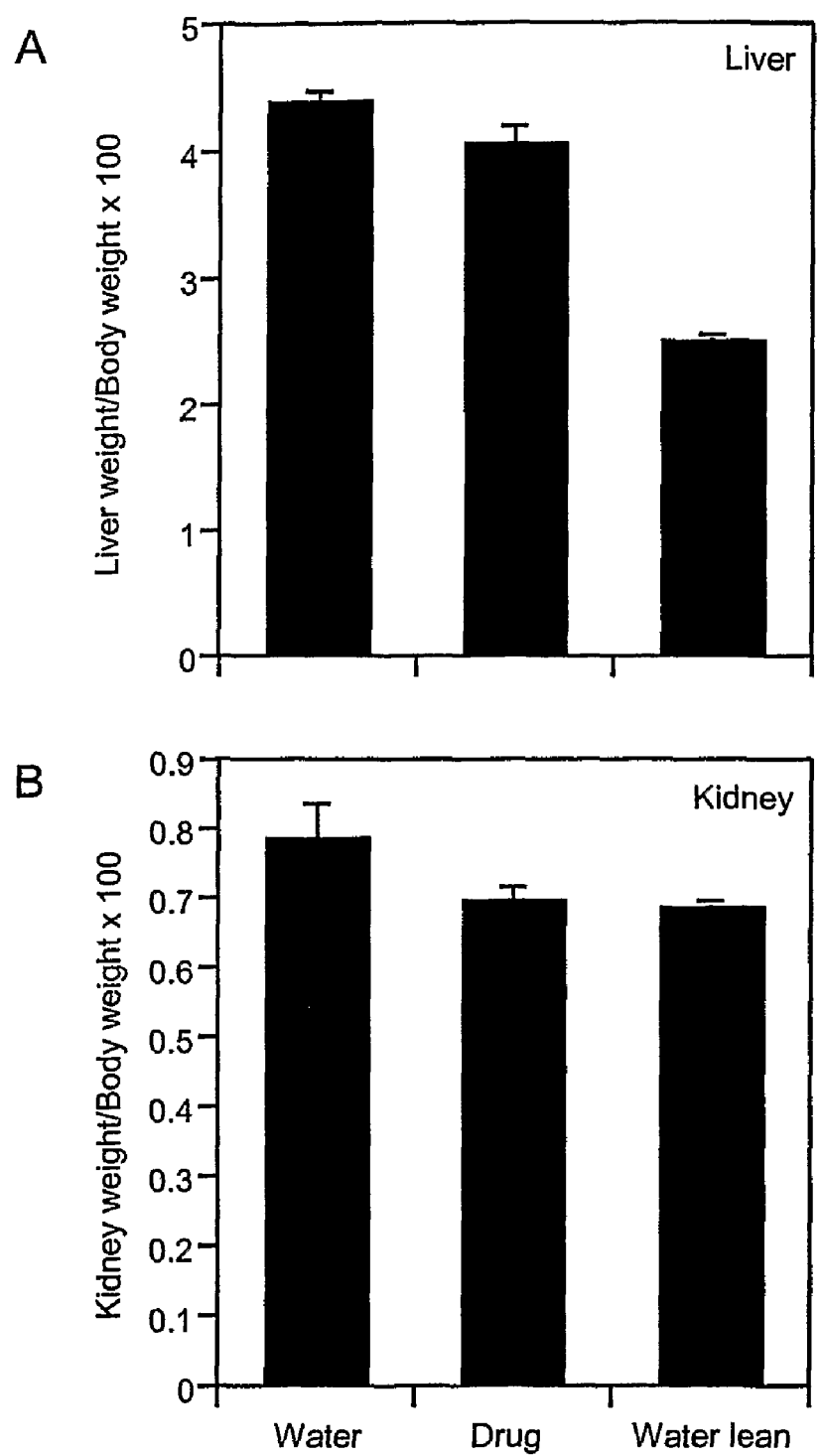

D-threo-1-(3',4'-ethylenedioxy)phenyl-2-nonanoylamino-3-pyrrolidino-1-propanol decreased relative kidney and liver weights in ZDF rats, a symptom associated with diabetes. After 6 weeks of treatment with drug or water, livers (FIG. 5a) and kidneys FIG. 5b) were dissected and weighed. (N=6 rats per group±SEM). The results are presented as a percentage of total body weight. Lean rats given water were used as a control.

Example 4

Figure 6:
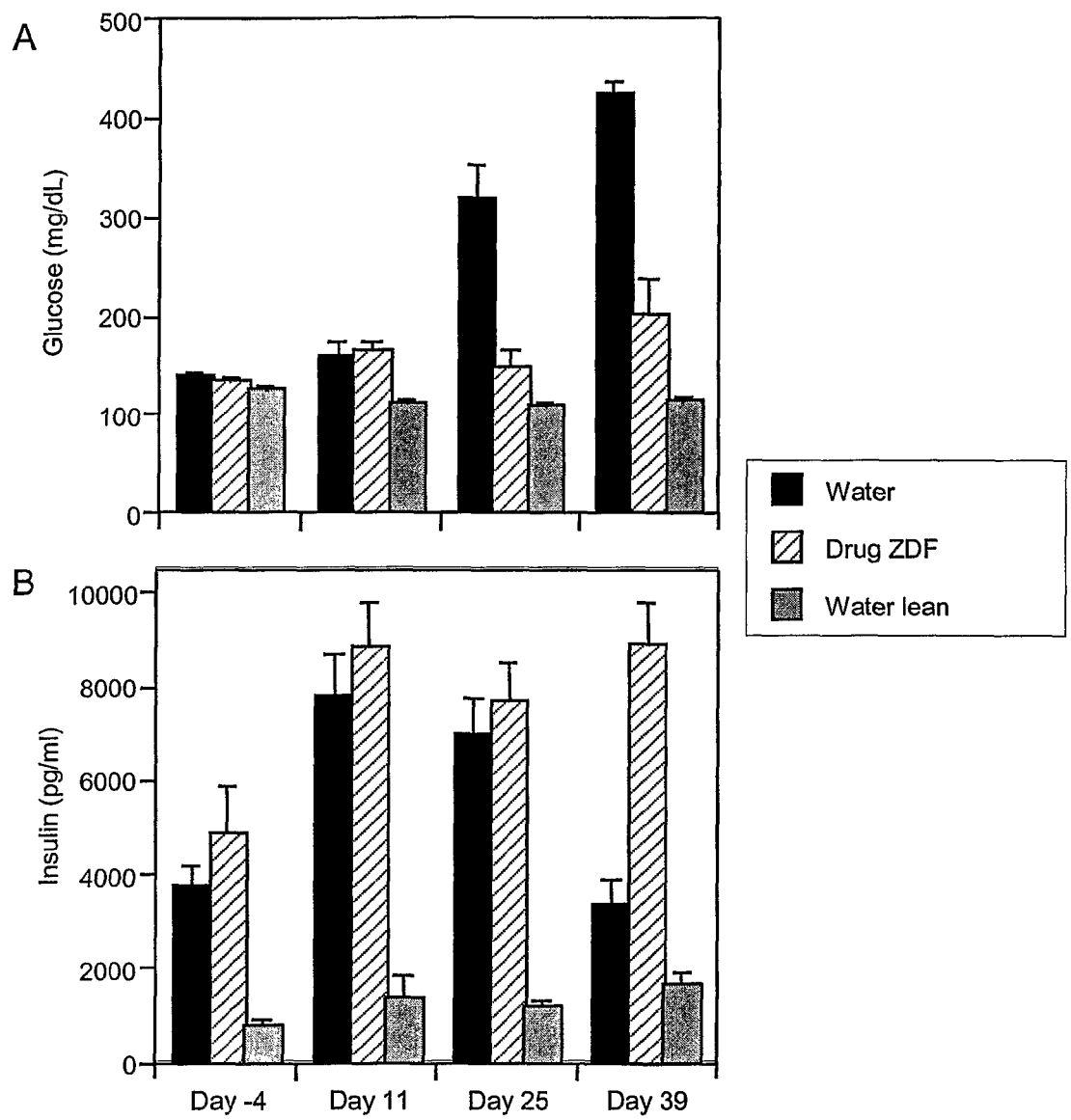

Decrease in Blood Glucose Levels and Concomitant Maintenance of Blood Insulin levels in ZDF Rats ZDF rats were treated daily with 75 mg/kg of D-threo-1-(3',4'-ethylenedioxy)phenyl-2-nonanoylamino-3-pyrrolidino-1-propanol or water. Lean control rats were given water. Four days before, and at day 11, 25, and 39 after initiation of treatment, blood was collected by tail vein nick between 8 and 9 AM, and glucose was measured using an Accu-Chek Compact Meter (Roche Diagnostics Corp., Indianapolis, Ind.). Blood was also collected by retroorbital plexus puncture at the same time as the tail nick. Insulin levels in plasma were assayed by an ELISA kit (Crystal Chem, Inc., Downers Grove, Ill.). (N=6 rats per group±SEM). The results showed that D-threo-1-(3',4'-ethylenedioxy)phenyl-2-nonanoylamino-3-pyrrolidino-1-propanol decreased blood glucose levels in ZDF rats (FIG. 6a). The drug also maintained insulin levels in the same rats (FIG. 6b).

Example 5

Glucose Tolerance in ZDF Rats

Figure 7:
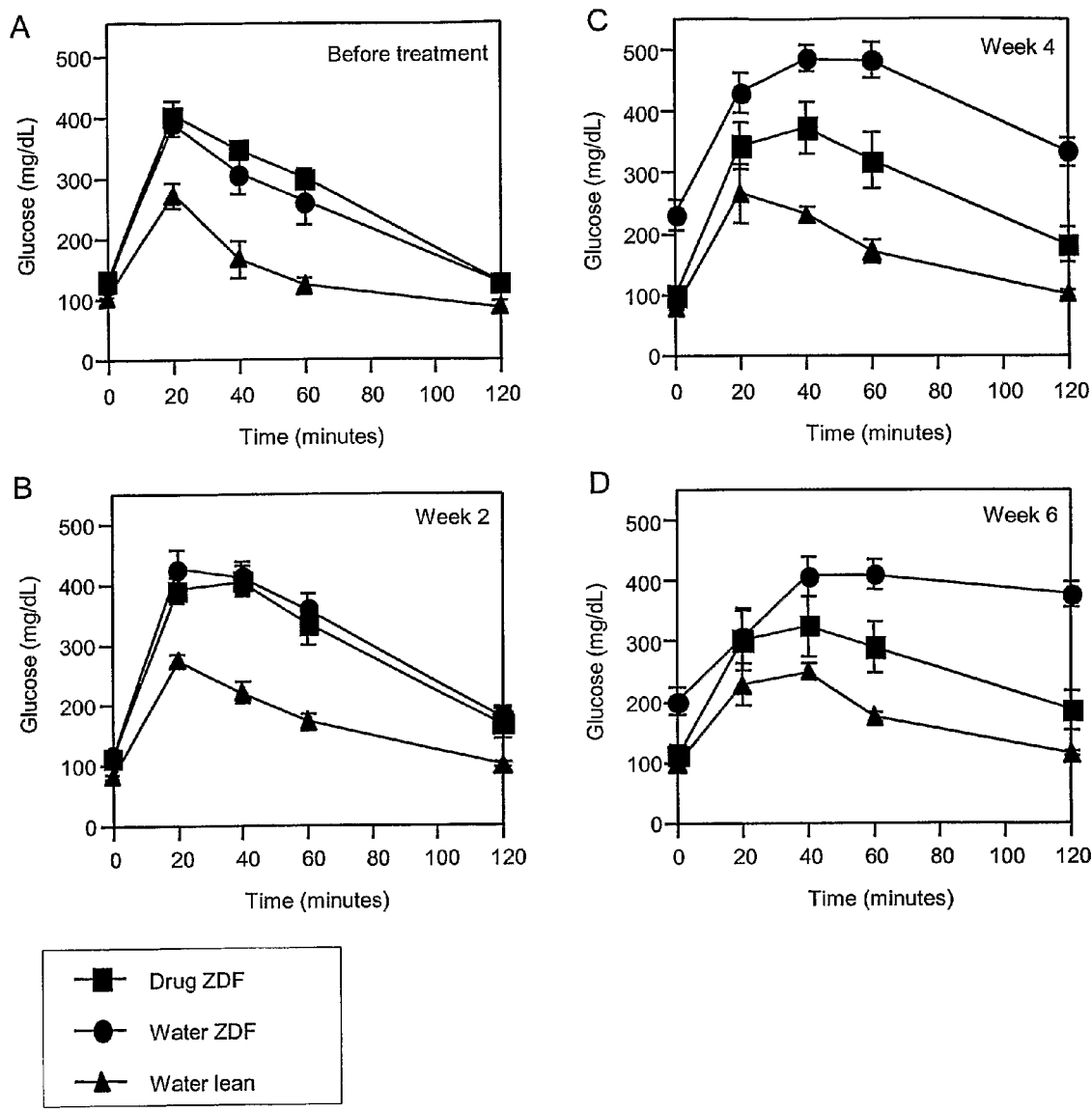
FIG. 7 is a graph showing the results of a glucose tolerance test. Each panel compares glucose blood levels after a glucose challenge at a different time point relative to the start of therapy. Three groups of rats were studied: ZDF rats treated with a glucosylceramide synthase inhibitor (i.e., drug); ZDF rats given water instead of drug; and lean rats given water.

Glucose tolerance tests were performed on each group of rats before treatment and 2, 4, and 6 weeks after the initiation of treatment with 75 mg/kg of D-threo-1-(3',4'-ethylenedioxy)phenyl-2-nonanoylamino-3-pyrrolidino-1-propanol. The drug was administered daily by oral gavage. Animals were fasted overnight prior to each test, and baseline glucose levels were measured just before each injection. The animals were injected intraperitoneally with glucose solution (2 g/kg) (Sigma, St. Louis, Mo.), and blood was collected by tail vein nick at 20, 40, 60, and 120 minutes after the injection. Glucose levels were measured using an Accu-Chek Compact Meter (Roche Diagnostics Corp., Indianapolis, Ind.). (N=6 rats per group±SEM). The results showed that after 4 and 6 weeks of treatment with the drug glucose tolerance improved in ZDF rats (FIG. 7).

Example 6

Glycated Hemoglobin Levels in ZDF Rats

Figure 8:
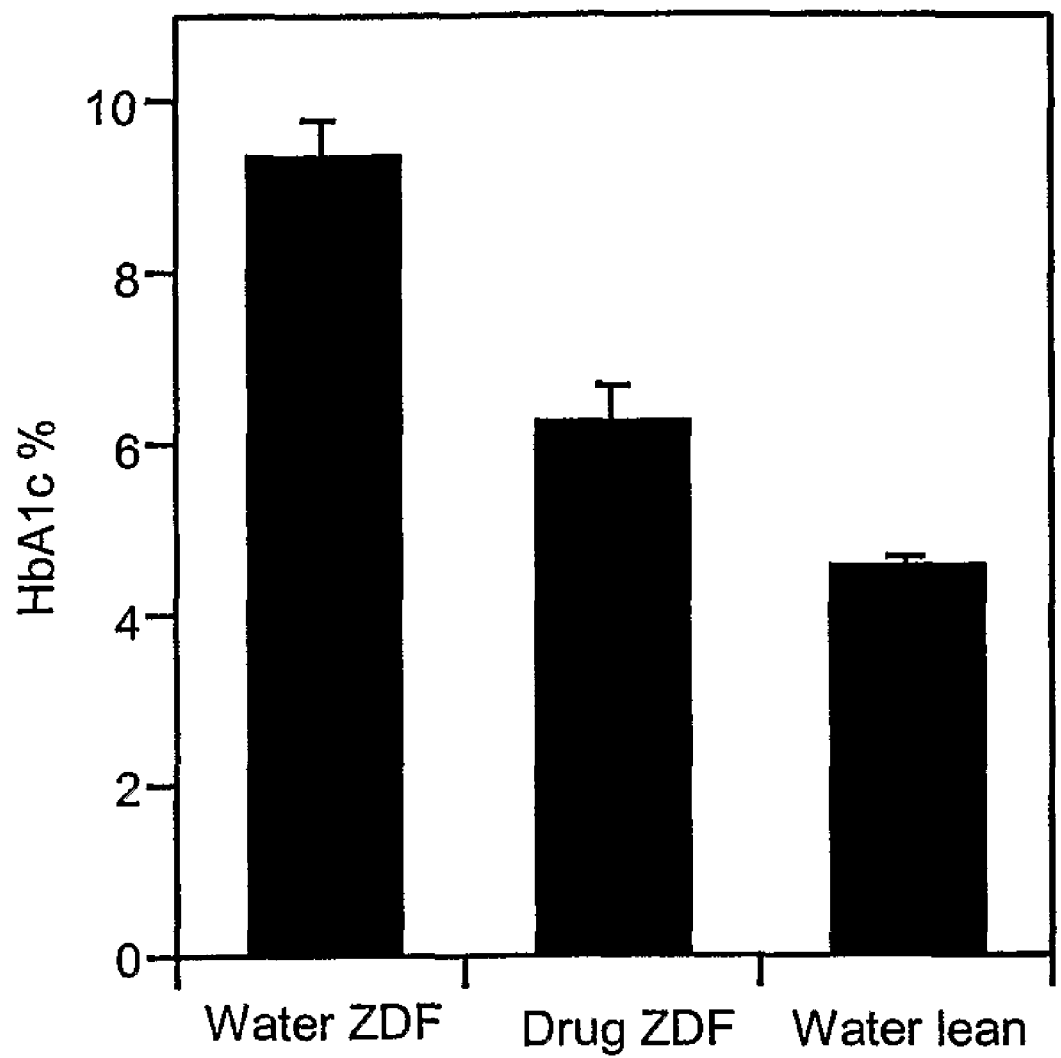
FIG. 8 is a graph showing levels of glycated hemoglobin in three groups of rats: ZDF rats treated with a glucosylceramide synthase inhibitor (i.e., drug); ZDF rats given water instead of drug; and lean rats given water.

Glycated Hemoglobin (HbA1c) levels were measured as another indicator of blood glucose levels in each group of rats. After six weeks of treatment with 75 mg/kg of D-threo-1-(3',4'-ethylenedioxy)phenyl-2-nonanoylamino-3-pyrrolidino-1-propanol administered daily by oral gavage, the levels of HbA1c in the blood were measured using a hand-held A1C Now® monitor (Metrika, Inc., Sunnyvale, Calif.). (N=6 rats per group±SEM). The results showed that the drug reduced HbAc1 levels in ZDF rats (FIG. 8).

Example 7

Insulin Receptor Phosphorylation in Muscle Tissue of ZDF Rats

Figure 9:
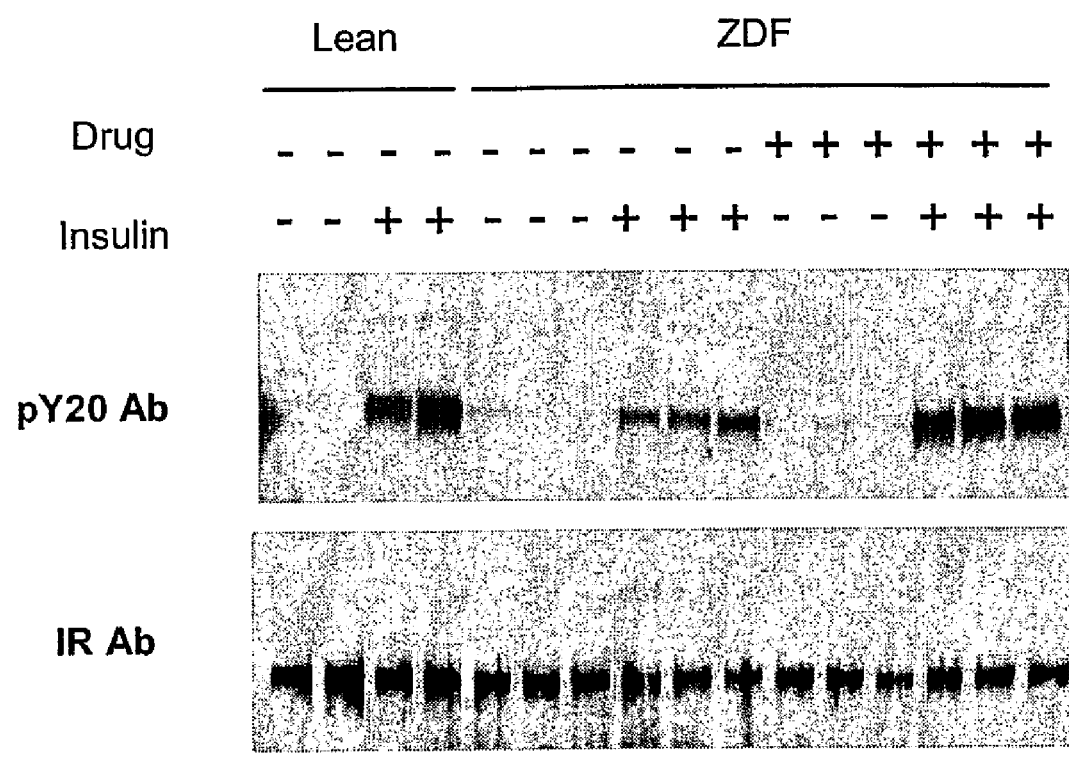
FIG. 9 is a Western blot of rat muscle cell homogenates immunoprecipitated with an insulin receptor antibody. The top panel shows phosphorylation of the insulin receptor in ZDF rats with or without injected human insulin, and with or without a glucosylceramide synthase inhibitor. Insulin receptor from a normal lean rat, with or without, injected human insulin is also shown. The lower panel shows levels of insulin receptor present in each sample.

ZDF rats treated with 75 mg/kg of D-threo-1-(3',4'-ethylenedioxy)phenyl-2-nonanoylamino-3-pyrrolidino-1-propanol (administered daily by oral gavage) for six weeks along with control group rats, were fasted overnight. The following morning the anesthetized rats were injected with human insulin (Humulin, 5U) (Eli Lily and Company, Indianapolis, Ind.) into the hepatic portal vein. Quadriceps muscle was harvested 2 minutes after injection and immediately frozen in liquid nitrogen. Insulin receptor (IR) was immunoprecipitated from muscle homogenates using an anti-IRβ antibody (IR Ab) (Santa Cruz Biotechnology Inc., Santa Cruz, Calif.), and then the immunoprecipitates were analyzed by immunoblotting using either an anti-phosphotyrosine antibody (pY20 Ab) (BD Bioscience, San Diego, Calif.), to measure phosphorylation levels, or using the anti-IRβ antibody (IR Ab) (Santa Cruz Biotechnology Inc., Santa Cruz, Calif.), to measure IR protein levels. The blots were visualized using chemiluminescence (ECL Western Kit, Amersham Biosciences, Piscataway, N.J.) and exposed to X-ray film. The results showed that the drug increased phosphorylation of the insulin receptor compared to the untreated control group and thus suggests that treatment with the drug enhances IR signaling capability in the ZDF rat after being stimulated with insulin (FIG. 9).

Example 8

Figure 10:
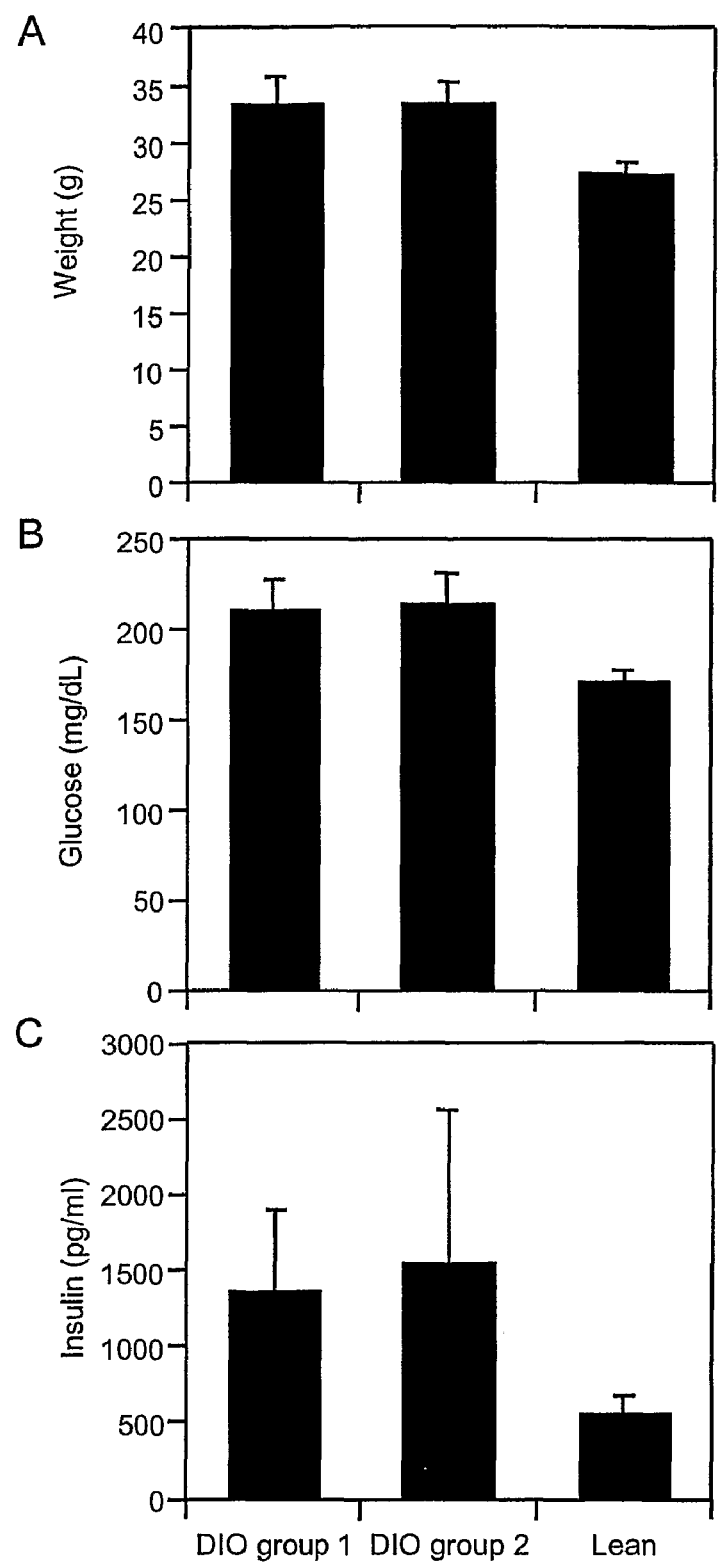
FIG. 10 is a graph showing physical parameters of 2 groups of diet induced obese mice (DIO) and a lean normal control.

Physiological Parameters in a Diet Induced Obese (DIO) Mouse Model of Type 2 Diabetes Male C57BL/6J mice at age 4 weeks were purchased from The Jackson Laboratory (Bar Harbor, Me.). They were housed at 20-24° C. with a 12 hour light:dark cycle. The mice were acclimatized in house for a week prior to being placed on the diet. One group of mice was fed with a high fat diet (D12451i 45% kcal) (Research Diets, Inc., New Brunswick, N.J.). A second group of mice was fed with regular chow (Purina 5K52 6%) (Purina Mills, LLC, St. Louis Mo.). Body weights were measured weekly. The mice were on the diet for 7 weeks, then postprandial blood glucose and insulin levels were measured. Those mice on the high fat diet who became obese and exhibited moderate hyperglycemia and hyperinsulinemia were selected for further study and divided into a control and treatment group. The treated and control groups were matched in terms of average body weights, glucose and insulin levels. The mice fed with regular chow were used as lean controls. The weight, glucose and insulin levels for the 2 groups of DIO mice and the lean controls are shown in FIG. 10.

Figure 11:
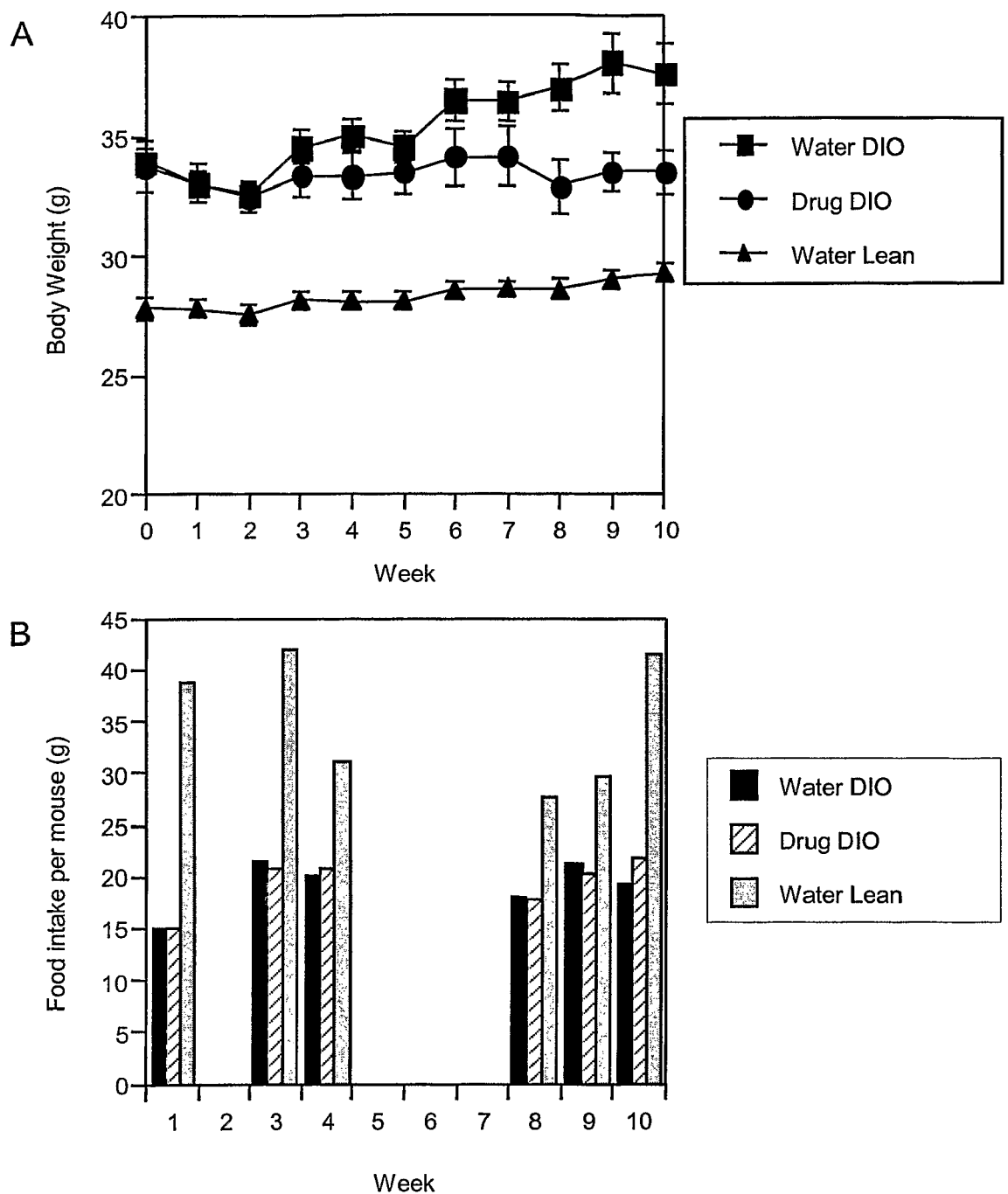

The treatment group were orally gavaged with 125 mg/kg/day of D-threo-1-(3',4'-ethylenedioxy)phenyl-2-nonanoylamino-3-pyrrolidino-1-propanol for 10 weeks. The control group were orally gavaged with water for 10 weeks. Body weight and food intake were monitored weekly. (N=10 mice per group±SEM). The drug did not affect food consumption (FIG. 11b), but decreased body weight gain in DIO mice (FIG. 11a).

Example 9

TNF-α Levels in DIO Mice

Figure 12:
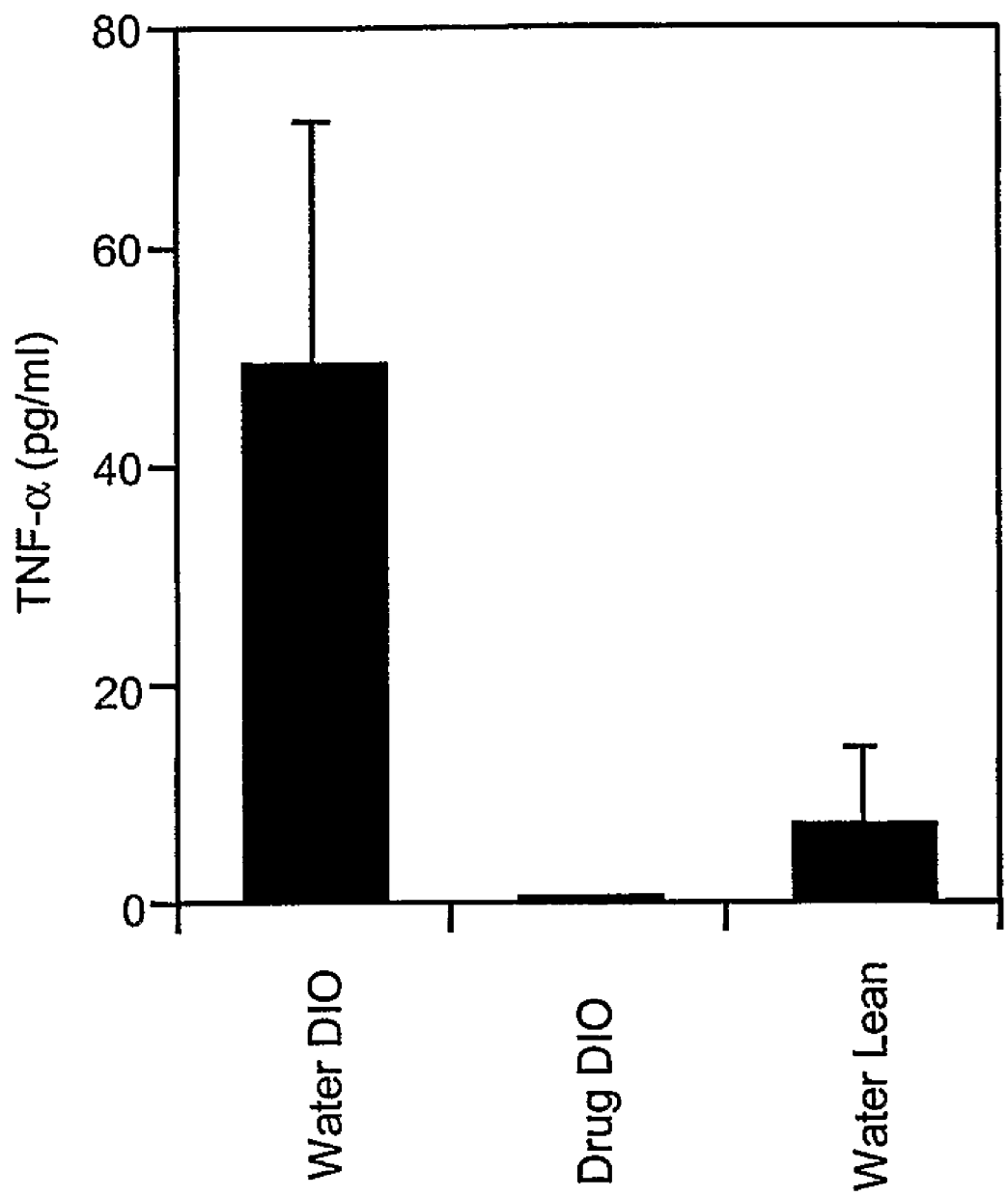
FIG. 12 is a graph showing plasma TNF-α levels in three groups of mice: DIO mice treated with a glucosylceramide synthase inhibitor (i.e., drug); DIO mice given water instead of drug; and lean mice given water.
Figure 13:
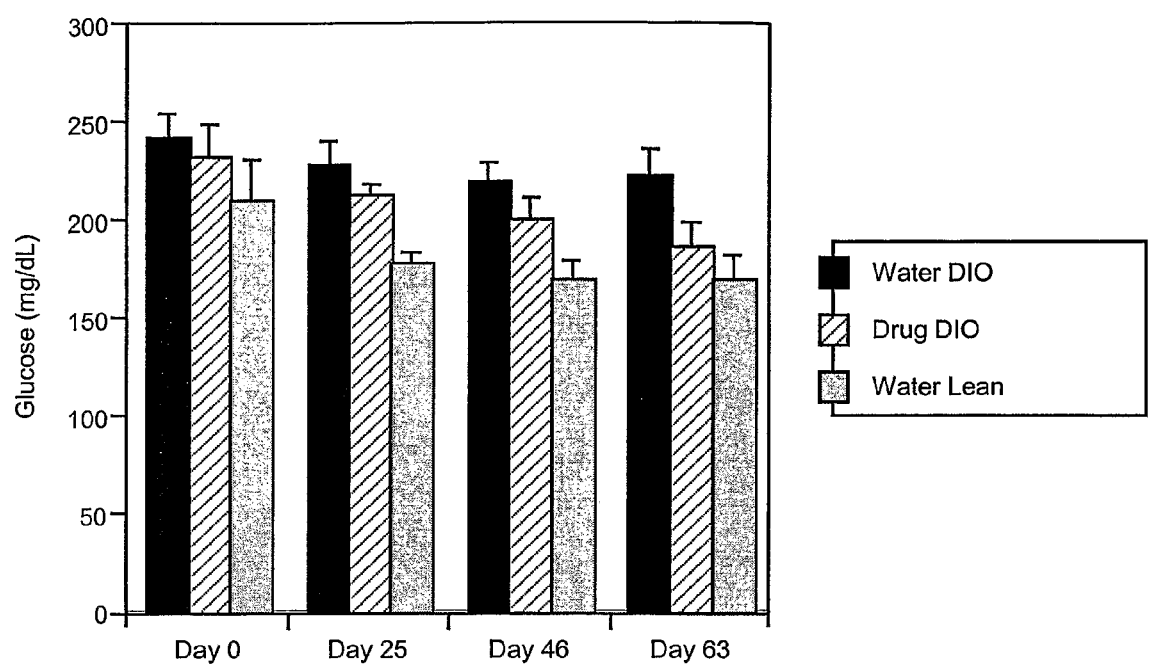
FIG. 13 is a graph showing blood glucose levels over time in three groups of mice: DIO mice treated with a glucosylceramide synthase inhibitor (i.e., drug); DIO mice given water instead of drug; and lean mice given water.

Nine weeks after the initiation of treatment (administered daily by oral gavage at 125 mg/kg), blood was collected by retroorbital plexus puncture and TNF-α was measured in plasma using an ELISA kit (R&D Systems). (N=10 mice per group±SEM). The results showed that treatment with D-threo-1-(3',4'-ethylenedioxy)phenyl-2-nonanoylamino-3-pyrrolidino-1-propanol inhibited TNF-α levels in DIO mice (FIG. 12).

Example 10

Blood Glucose Levels in DIO Mice

Blood was collected by tail vein nick on day 0, 25, 46, and 63 after initiation of treatment (administered daily by oral gavage at 125 mg/kg). Samples were collected between 8 and 9 AM, and glucose was measured using an Accu-Chek Compact® Meter (Roche Diagnostics Corp., St. Louis, Mo.). (N=10 mice per group±SEM). The results showed that D-threo-1-(3',4'-ethylenedioxy)phenyl-2-nonanoylamino-3- pyrrolidino-1-propanol decreased blood glucose levels in DIO mice compared to untreated controls and the difference increased over time.

Example 11

Insulin Levels in DIO Mice

Figure 14:
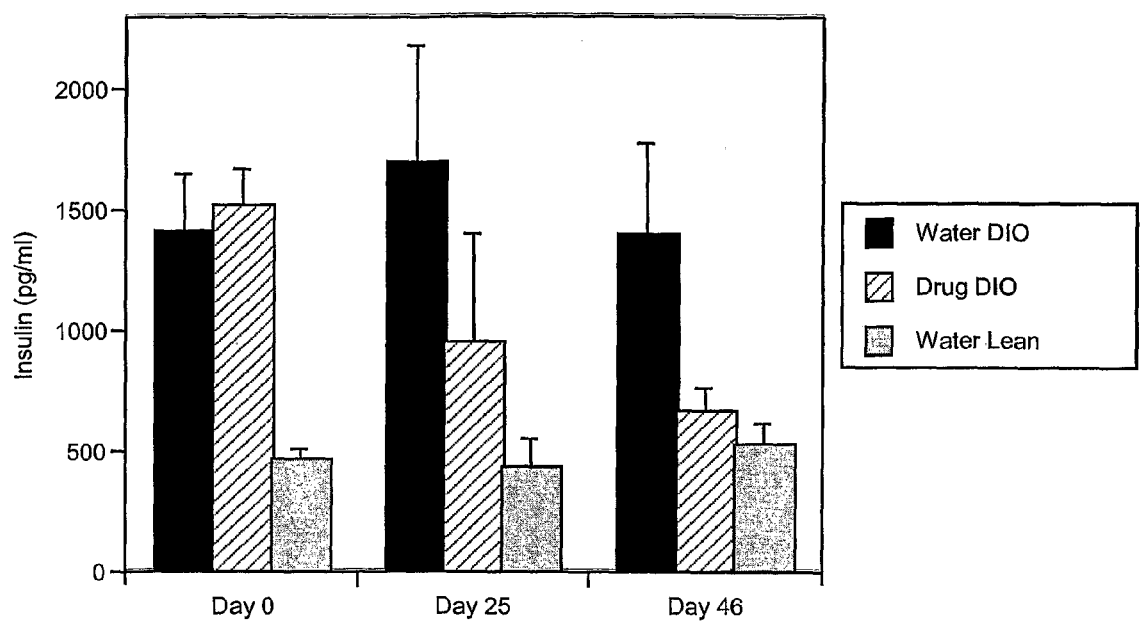
FIG. 14 is a graph showing insulin levels overtime in three groups of mice: DIO mice treated with a glucosylceramide synthase inhibitor (i.e., drug); DIO mice given water instead of drug; and lean mice given water.

Blood was collected by retroorbital plexus puncture on day 0 and on day 25 and 46 after the initiation of treatment (administered daily by oral gavage at 125 mg/kg). Plasma insulin levels were measured by an ELISA kit (Crystal Chem. Inc., Downers Grove, Ill.). (N=10 mice per group±SEM). The results showed that D-threo-1-(3',4'-ethylenedioxy)phenyl-2-nonanoylamino-3-pyrrolidino-1-propanol decreased insulin levels in DIO mice compared to untreated controls (FIG. 14).

Example 12

Glucose Tolerance in DIO Mice

Figure 15:
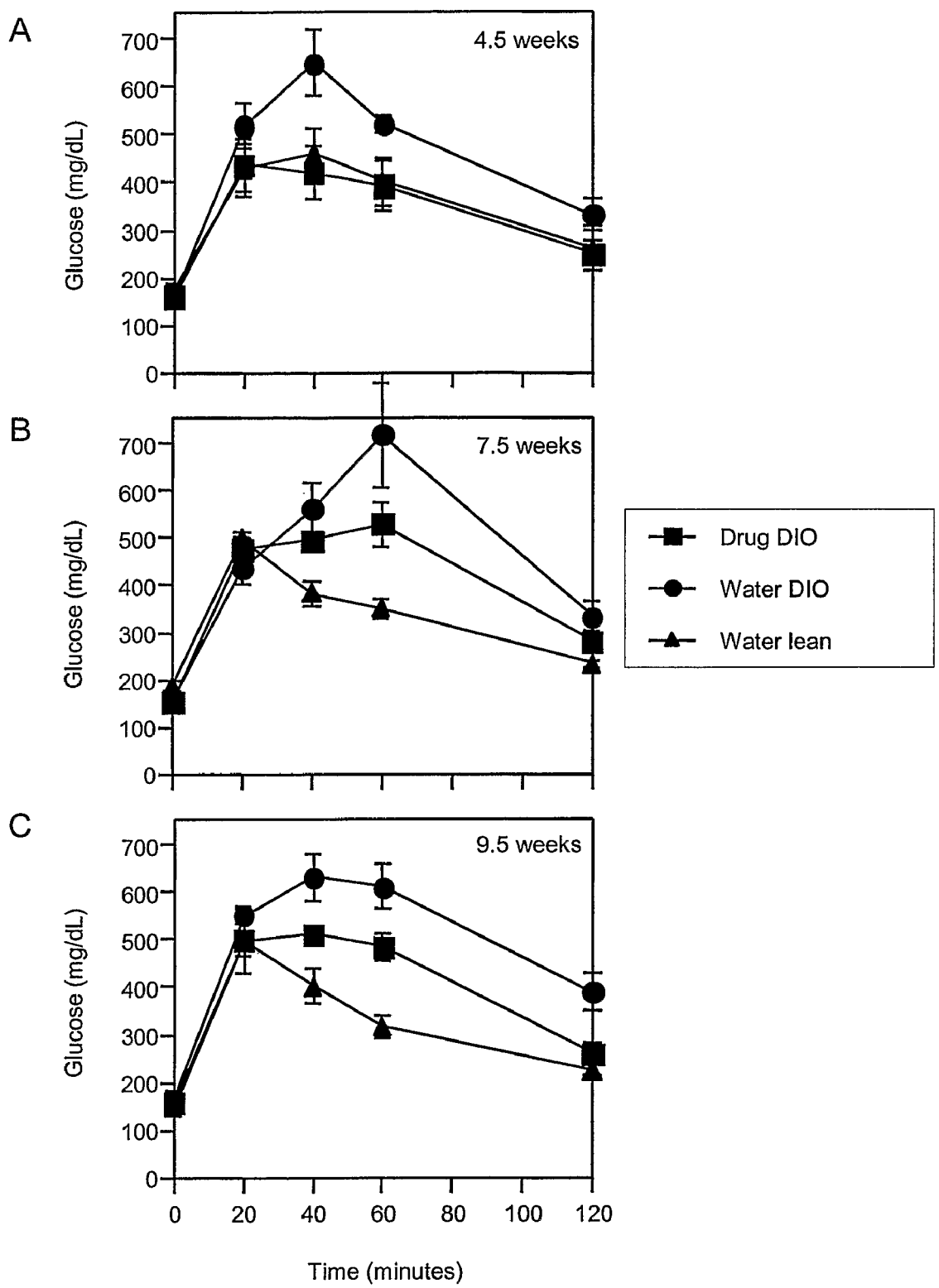
FIG. 15 is a graph showing the results of a glucose tolerance test. Each panel compares glucose blood levels after a glucose challenge at a different time point relative to the start of therapy. Three groups of mice were studied: DIO mice treated with a glucosylceramide synthase inhibitor (i.e., drug); DIO mice given water instead of drug; and lean mice given water.

Tests were performed 4.5, 7.5, and 9.5 weeks after the initiation of treatment (administered daily by oral gavage at 125 mg/kg). Animals were fasted overnight prior to each test. Baseline glucose levels were measured just before injection. The animals were injected intraperitoneally with glucose solution (2 g/kg, Sigma, St. Louis, Mo.), and blood was collected by tail vein nick at 20, 40, 60, and 120 minutes after injection. Glucose levels were measured using an Accu-Chek Compact Meter (Roche Diagnostics Corp., Indianapolis, Ind.). (N=10 mice per group±SEM). The results showed that D-threo-1-(3',4'-ethylenedioxy)phenyl-2-nonanoylamino-3-pyrrolidino-1-propanol improved glucose tolerance in DIO mice (FIG. 15).

Example 13

Glycated Hemoglobin Levels in DIO Mice

Figure 16:
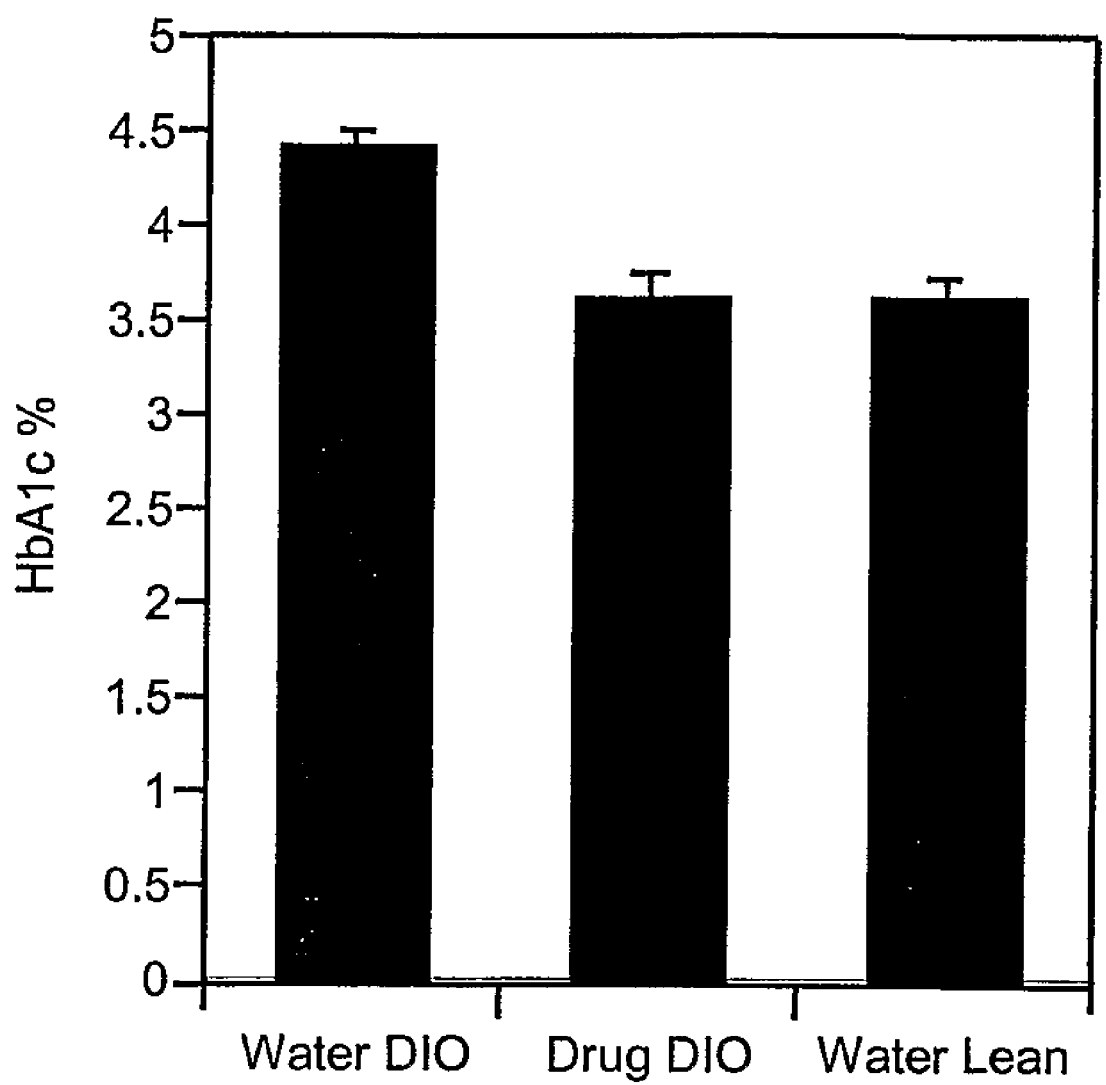
FIG. 16 is a graph showing levels of glycated hemoglobin in three groups of mice: DIO mice treated with a glucosylceramide synthase inhibitor (i.e., drug); DIO mice given water instead of drug; and lean mice given water.

Glycated Hemoglobin (HbA1c) levels were measured as another indicator of blood glucose levels in each group of mice. After ten weeks of treatment with D-threo-1-(3',4'-ethylenedioxy)phenyl-2-nonanoylamino-3-pyrrolidino-1-propanol, (administered daily by oral gavage at 125 mg/kg) the levels of glycated hemoglobin HbA1c in the blood were measured using a hand-held A1C Now® monitor (Metrika, Inc., Sunnyvale, Calif.). (N=10 mice per group±SEM). The results showed that the drug treatment normalized HbA1c levels to the level of the normal lean mice (FIG. 16).

All references cited herein are incorporated herein by reference in their entirety. To the extent publications and patents or patent applications incorporated by reference contradict the disclosure contained in the specification, the specification is intended to supercede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method of treating a subject having type 2 diabetes, the method comprising administering to the subject a therapeutically effective amount of a composition comprising a compound of Formula 1b, or a pharmaceutically acceptable salt thereof,

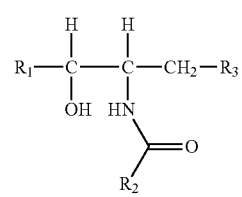

(Formula 1b)

where $R_1$ is an optionally substituted aromatic ring or an optionally substituted heterocycle; $R_2$ is an optionally substituted alkyl group; and $R_3$ is an optionally substituted tertiary cyclic amine,
with the proviso that $R_3$ is not morpholine.

2. The method of claim 1, wherein $R_1$ is an optionally substituted aromatic ring.

3. The method of claim 2, wherein $R_1$ is an optionally substituted phenyl group.

4. The method of claim 3, wherein $R_1$ is a phenyl group; $R_2$ is an alkyl group; and $R_3$ is a tertiary cyclic amine, and where the tertiary cyclic amine is not a morpholine group.

5. The method of claim 3, wherein $R_1$ is a substituted phenyl group.

6. The method of claim 5, wherein $R_1$ is (3',4'-ethylenedioxy)phenyl.

7. The method of claim 1, wherein $R_3$ is pyrrolidine.

8. The method of claim 1, wherein $R_2$ comprises at least 7 carbon atoms.

9. The method of claim 8, wherein $R_2$ is an optionally substituted $C_7$-$C_{18}$ alkyl group.

10. The method of claim 9, wherein $R_2$ is an optionally substituted $C_7$ alkyl group.

11. The method of claim 10, wherein $R_2$ is chosen from 1-(1-hydroxyheptyl) and 1-(6-hydroxyheptyl).

12. The method of claim 9, wherein $R_2$ is an optionally substituted $C_8$ alkyl group.

13. The method of claim 12, wherein $R_2$ is chosen from 1-(1-hydroxyoctyl) and 1-(7-hydroxyoctyl).

14. The method of claim 1, wherein the compound of Formula 1b is in the form of a free base.

15. The method of claim 1, wherein the compound of Formula 1b is in the form of a pharmaceutically acceptable salt.

16. The method of claim 15, wherein the pharmaceutically acceptable salt is chosen from citrate, tartrate, hydrochloride, hydrobromide, sulfate, hydrogen sulfate, phosphate, hydrogen phosphate, dihydrogenphosphate, acetate, succinate, methanesulfonate (mesylate) and p-toluenesulfonate (tosylate).

17. The method of claim 1, wherein the compound of Formula 1b is a D-threo isomer.

18. The method of claim 1, wherein the compound of Formula 1b is an L-threo isomer.

19. The method of claim 1, wherein the compound of Formula 1b is an L-erythro isomer.

20. The method of claim 1, wherein the compound of Formula 1b is a D-erythro isomer.

21. The method of claim 1, wherein the compound of Formula 1b is a tartrate salt, and wherein $R_1$ is D-threo-(3',4'-ethylenedioxy)phenyl, $R_3$ is pyrrolidine, and $R_2$ is a $C_7$ alkyl group.

22. The method of claim 1, wherein the compound of Formula 1b is a tartrate salt, and wherein $R_1$ is D-threo-(3',4'-ethylenedioxy)phenyl, $R_3$ is pyrrolidine, and $R_2$ is a $C_8$ alkyl group.

23. The method of claim 1, wherein the composition further comprises a pharmaceutically acceptable excipient.

24. The method of claim 1, wherein the compound of Formula 1b is administered orally.

25. The method of claim 1, wherein administration of the compound of Formula 1b to the subject decreases blood glucose levels in the subject compared to a subject not treated with the compound.

26. The method of claim 1, wherein administration of the compound of Formula 1b to the subject increases blood insulin levels in the subject compared to a subject not treated with the compound.

27. The method of claim 1, further comprising administering to the subject at least one compound chosen from a sulfonylurea, a metformin, an α-glucosidase inhibitor, troglitazone, glyburide, nateglinide, thiazolidiinedione and repaglinide.

28. The method of claim 1, wherein the compound of Formula 1b is 1-(3',4'-ethylenedioxy)phenyl-2-nonanoylamino-3-pyrrolidino-1-propanol or a salt thereof.

29. The method of claim 1, wherein the compound of Formula 1b is 1-(3',4'-ethylenedioxy)phenyl-2-octanoylamino-3-pyrrolidino-1-propanol or a salt thereof.

30. The method of claim 4, wherein $R_1$ is a substituted phenyl group.

31. The method of claim 30, wherein the substituted phenyl group is (3',4'-ethylenedioxy)phenyl.

32. The method of claim 4, wherein $R_3$ is pyrrolidine.

33. The method of claim 4, wherein $R_2$ comprises at least 7 carbon atoms.

34. The method of claim 33, wherein $R_2$ is a $C_7$-$C_{18}$ alkyl group.

35. The method of claim 34, wherein the alkyl group is a $C_7$ alkyl group.

36. The method of claim 33, wherein $R_2$ is a $C_8$ alkyl group.

37. The method of claim 4, wherein the compound is in the form of a free base.

38. The method of claim 4, wherein the compound is in the form of a pharmaceutically acceptable salt.

39. The method of claim 38, wherein the salt is chosen from citrate, tartrate hydrochloride, hydrobromide, sulfate, hydrogen sulfate, phosphate, hydrogen phosphate, dihydrogenphosphate, acetate, succinate, methanesulfonate (mesylate) and p-toluenesulfonate (tosylate).

40. The method of claim 4, wherein the compound is a D-threo isomer.

41. The method of claim 4, wherein the compound is a L-threo isomer.

42. The method of claim 4, wherein the compound is a L-erythro isomer.

43. The method of claim 4, wherein the compound is a D-erythro isomer.

44. The method of claim 4, wherein the compound is a tartrate salt and wherein $R_1$ is D-threo-(3',4'-ethylonedioxy)phenyl, $R_3$ is pyrrolidine, and $R_2$ is a $C_7$ alkyl group.

45. The method of claim 4, wherein the compound is a tartrate salt, and wherein the $R_1$ is D-threo-(3'4'-ethylenedioxy)phenyl, $R_3$ is pyrrolidine, and $R_2$ is a $C_8$ alkyl group.

46. The method of claim 4, wherein the composition further comprises a pharmaceutically acceptable excipient.

47. The method of claim 4, wherein the compound is administered orally.

48. The method of claim 4, wherein administration of the compound to the subject decreases blood glucose levels in the subject compared to a subject not treated with the compound.

49. The method of claim 4, wherein administration of the compound to the subject increases blood insulin levels in the subject compared to a subject not treated with the compound.

50. The method of claim 4, further comprising administering to the subject at least one compound chosen from a sulfonylurea, a metformin, an α-glucosidase inhibitor, troglitazone, glyburide, nateglinide, thiazolidiinedione and repaglinide.

* * * * *